(12) United States Patent
Bhattacharya et al.

(10) Patent No.: US 11,119,103 B1
(45) Date of Patent: Sep. 14, 2021

(54) SEROLOGICAL ASSAYS FOR SARS-COV-2

(71) Applicant: Arizona Board of Regents on Behalf of the University of Arizona, Tucson, AZ (US)

(72) Inventors: Deepta Bhattacharya, Tucson, AZ (US); Ryan Sprissler, Tucson, AZ (US); Janko Nikolich-Zugich, Tucson, AZ (US); Matthew Kaplan, Tucson, AZ (US); Tyler Ripperger, Tucson, AZ (US); Jennifer Uhrlaub, Tucson, AZ (US); Makiko Watanabe, Tucson, AZ (US); Rachel Wong, Tucson, AZ (US)

(73) Assignee: Arizona Board of Regents on Behalf of the University of Arizona, a body corporate, Tucson, AZ (US)

( * ) Notice: Subject to any disclaimer, the term of this patent is extended or adjusted under 35 U.S.C. 154(b) by 0 days.

(21) Appl. No.: 16/900,798

(22) Filed: Jun. 12, 2020

(51) Int. Cl.
*G01N 33/569* (2006.01)

(52) U.S. Cl.
CPC . *G01N 33/56983* (2013.01); *G01N 2333/165* (2013.01); *G01N 2469/20* (2013.01)

(58) Field of Classification Search
None
See application file for complete search history.

(56) References Cited

U.S. PATENT DOCUMENTS 7,220,852 B1 * 5/2007 Rota ............... A61K 39/215
435/235.1
2007/0270361 A1 * 11/2007 Lu ..................... A61K 39/42
514/44 R

OTHER PUBLICATIONS

Yellapu et al. (Vaccines. Oct. 8, 2020; 8: 591).*
Sela-Culang et al. (Frontiers in Immunology. 2013; 4: 302).*
Jaimes et al. (Journal of Molecular Biology (Apr. 19, 2020) 432, 3309-3325).*
Zhao et al. (Clinical Infectious Diseases. Mar. 28, 2020; 71: 2027-2034).*
Jaaskelainen et al (Eurosurveillance. (May 7, 2020); 25 (18): 2000603).*
Hsueh et al. (Clinical Microbiology and Infectious Diseases. 2004; 10: 1062-1066).*
"Liaison® SARS-CoV-2 S1/S2 IgG: The fully automated serology test for the detection of SARS-CoV-2 IgG", DiaSorin S.p. A (ID: Infectious Disease), 4 pp.
Assis et al. (Apr. 17, 2020) "Analysis of SARS-CoV-2 Antibodies in COVID-19 Convalescent Plasma using a Coronavirus Antigen Microarray," *bioRxiv* (Int'l license info: https://creativecommons.org/licenses/by-nd/4.0/legalcode), 21 pp (pre-publication).
Okba (Jul. 2020) "Severe Acute Respiratory Syndrome Coronavirus 2-Specific Antibody Responses in Coronavirus Disease Patients," *Centers for Disease Control and Prevention: Research*, vol. 26, No. 7, 9 pp.
Stadlbauer et al. (2020) "SARS-CoV-2 Seroconversion in Humans: A Detailed Protocol for a Serological Assay, Antigen Production, and Test Setup," *Current Protocols in Microbiology* e100, vol. 57, 15 pp.

* cited by examiner

*Primary Examiner* — Shanon A. Foley
(74) *Attorney, Agent, or Firm* — Lathrop GPM LLP

(57) ABSTRACT

Provided herein is a test system comprising severe acute respiratory syndrome coronavirus 2 (SARS-CoV-2) receptor binding domain (RBD) antigen, SARS-CoV-2 S2 antigen, and binding moieties that specifically bind to human IgG, human IgA, and human IgM. Also provided are methods of detecting SARS-CoV-2 antibodies in a sample using the test system.

Figure 1:
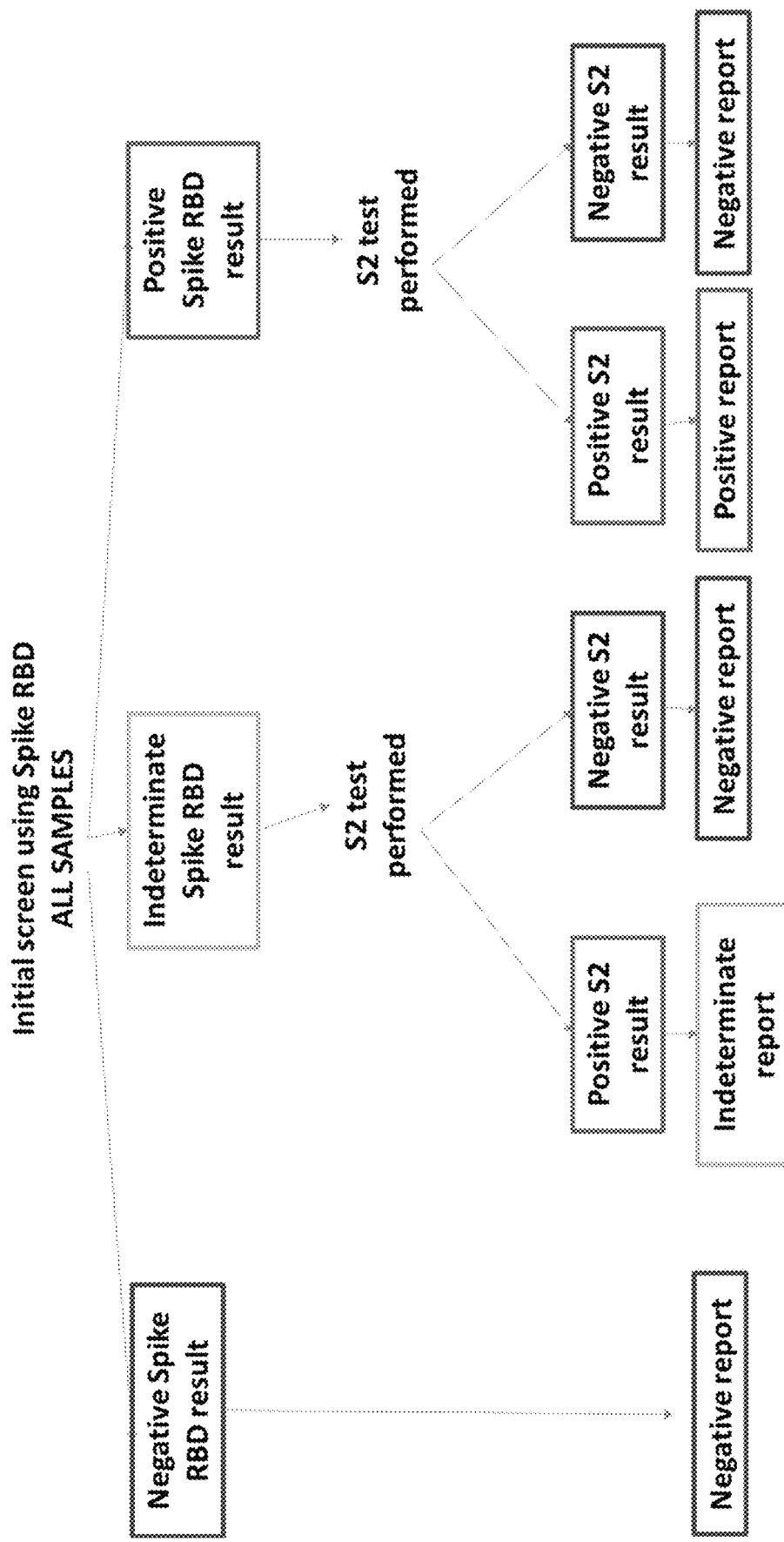

30 Claims, 9 Drawing Sheets
Specification includes a Sequence Listing.

FIG. 7

SEQUENCE LISTING

<160> NUMBER OF SEQ ID NOS: 18

<210> SEQ ID NO 1
<211> LENGTH: 252
<212> TYPE: PRT
<213> ORGANISM: Artificial Sequence
<220> FEATURE:
<223> OTHER INFORMATION: Polypeptide

<400> SEQUENCE: 1

```
Met Phe Val Phe Leu Val Leu Leu Pro Leu Val Ser Ser Gln Arg Val
1               5                   10                  15

Gln Pro Thr Glu Ser Ile Val Arg Phe Pro Asn Ile Thr Asn Leu Cys
            20                  25                  30

Pro Phe Gly Glu Val Phe Asn Ala Thr Arg Phe Ala Ser Val Tyr Ala
        35                  40                  45

Trp Asn Arg Lys Arg Ile Ser Asn Cys Val Ala Asp Tyr Ser Val Leu
    50                  55                  60

Tyr Asn Ser Ala Ser Phe Ser Thr Phe Lys Cys Tyr Gly Val Ser Pro
65                  70                  75                  80

Thr Lys Leu Asn Asp Leu Cys Phe Thr Asn Val Tyr Ala Asp Ser Phe
                85                  90                  95

Val Ile Arg Gly Asp Glu Val Arg Gln Ile Ala Pro Gly Gln Thr Gly
            100                 105                 110

Lys Ile Ala Asp Tyr Asn Tyr Lys Leu Pro Asp Asp Phe Thr Gly Cys
        115                 120                 125

Val Ile Ala Trp Asn Ser Asn Asn Leu Asp Ser Lys Val Gly Gly Asn
    130                 135                 140

Tyr Asn Tyr Leu Tyr Arg Leu Phe Arg Lys Ser Asn Leu Lys Pro Phe
145                 150                 155                 160

Glu Arg Asp Ile Ser Thr Glu Ile Tyr Gln Ala Gly Ser Thr Pro Cys
                165                 170                 175

Asn Gly Val Glu Gly Phe Asn Cys Tyr Phe Pro Leu Gln Ser Tyr Gly
            180                 185                 190

Phe Gln Pro Thr Asn Gly Val Gly Tyr Gln Pro Tyr Arg Val Val Val
        195                 200                 205

Leu Ser Phe Glu Leu Leu His Ala Pro Ala Thr Val Cys Gly Pro Lys
    210                 215                 220

Lys Ser Thr Asn Leu Val Lys Asn Lys Cys Val Asn Phe Gly Leu Asn
225                 230                 235                 240

Asp Ile Phe Glu Ala Gln Lys Ile Glu Trp His Glu
                245                 250
```

<210> SEQ ID NO 2
<211> LENGTH: 258
<212> TYPE: PRT
<213> ORGANISM: Artificial Sequence
<220> FEATURE:
<223> OTHER INFORMATION: Polypeptide

<400> SEQUENCE: 2

```
Met Phe Val Phe Leu Val Leu Leu Pro Leu Val Ser Ser Gln Arg Val
1               5                   10                  15

Gln Pro Thr Glu Ser Ile Val Arg Phe Pro Asn Ile Thr Asn Leu Cys
            20                  25                  30

Pro Phe Gly Glu Val Phe Asn Ala Thr Arg Phe Ala Ser Val Tyr Ala
        35                  40                  45

Trp Asn Arg Lys Arg Ile Ser Asn Cys Val Ala Asp Tyr Ser Val Leu
    50                  55                  60

Tyr Asn Ser Ala Ser Phe Ser Thr Phe Lys Cys Tyr Gly Val Ser Pro
65                  70                  75                  80

Thr Lys Leu Asn Asp Leu Cys Phe Thr Asn Val Tyr Ala Asp Ser Phe
                85                  90                  95
```

-continued

```
Val Ile Arg Gly Asp Glu Val Arg Gln Ile Ala Pro Gly Gln Thr Gly
                100                 105                 110

Lys Ile Ala Asp Tyr Asn Tyr Lys Leu Pro Asp Asp Phe Thr Gly Cys
            115                 120                 125

Val Ile Ala Trp Asn Ser Asn Asn Leu Asp Ser Lys Val Gly Gly Asn
        130                 135                 140

Tyr Asn Tyr Leu Tyr Arg Leu Phe Arg Lys Ser Asn Leu Lys Pro Phe
145                 150                 155                 160

Glu Arg Asp Ile Ser Thr Glu Ile Tyr Gln Ala Gly Ser Thr Pro Cys
                165                 170                 175

Asn Gly Val Glu Gly Phe Asn Cys Tyr Phe Pro Leu Gln Ser Tyr Gly
            180                 185                 190

Phe Gln Pro Thr Asn Gly Val Gly Tyr Gln Pro Tyr Arg Val Val Val
        195                 200                 205

Leu Ser Phe Glu Leu Leu His Ala Pro Ala Thr Val Cys Gly Pro Lys
210                 215                 220

Lys Ser Thr Asn Leu Val Lys Asn Lys Cys Val Asn Phe Gly Leu Asn
225                 230                 235                 240

Asp Ile Phe Glu Ala Gln Lys Ile Glu Trp His Glu His His His His
                245                 250                 255

His His

<210> SEQ ID NO 3
<211> LENGTH: 528
<212> TYPE: PRT
<213> ORGANISM: Artificial Sequence
<220> FEATURE:
<223> OTHER INFORMATION: Polypeptide

<400> SEQUENCE: 3

Ser Val Ala Ser Gln Ser Ile Ile Ala Tyr Thr Met Ser Leu Gly Ala
1               5                   10                  15

Glu Asn Ser Val Ala Tyr Ser Asn Asn Ser Ile Ala Ile Pro Thr Asn
            20                  25                  30

Phe Thr Ile Ser Val Thr Thr Glu Ile Leu Pro Val Ser Met Thr Lys
        35                  40                  45

Thr Ser Val Asp Cys Thr Met Tyr Ile Cys Gly Asp Ser Thr Glu Cys
    50                  55                  60

Ser Asn Leu Leu Leu Gln Tyr Gly Ser Phe Cys Thr Gln Leu Asn Arg
65                  70                  75                  80

Ala Leu Thr Gly Ile Ala Val Glu Gln Asp Lys Asn Thr Gln Glu Val
                85                  90                  95

Phe Ala Gln Val Lys Gln Ile Tyr Lys Thr Pro Pro Ile Lys Asp Phe
            100                 105                 110

Gly Gly Phe Asn Phe Ser Gln Ile Leu Pro Asp Pro Ser Lys Pro Ser
        115                 120                 125

Lys Arg Ser Phe Ile Glu Asp Leu Leu Phe Asn Lys Val Thr Leu Ala
    130                 135                 140

Asp Ala Gly Phe Ile Lys Gln Tyr Gly Asp Cys Leu Gly Asp Ile Ala
145                 150                 155                 160

Ala Arg Asp Leu Ile Cys Ala Gln Lys Phe Asn Gly Leu Thr Val Leu
                165                 170                 175

Pro Pro Leu Leu Thr Asp Glu Met Ile Ala Gln Tyr Thr Ser Ala Leu
            180                 185                 190

Leu Ala Gly Thr Ile Thr Ser Gly Trp Thr Phe Gly Ala Gly Ala Ala
```

```
                195                 200                 205
Leu Gln Ile Pro Phe Ala Met Gln Met Ala Tyr Arg Phe Asn Gly Ile
            210                 215                 220

Gly Val Thr Gln Asn Val Leu Tyr Glu Asn Gln Lys Leu Ile Ala Asn
225                 230                 235                 240

Gln Phe Asn Ser Ala Ile Gly Lys Ile Gln Asp Ser Leu Ser Ser Thr
                245                 250                 255

Ala Ser Ala Leu Gly Lys Leu Gln Asp Val Val Asn Gln Asn Ala Gln
            260                 265                 270

Ala Leu Asn Thr Leu Val Lys Gln Leu Ser Ser Asn Phe Gly Ala Ile
            275                 280                 285

Ser Ser Val Leu Asn Asp Ile Leu Ser Arg Leu Asp Lys Val Glu Ala
290                 295                 300

Glu Val Gln Ile Asp Arg Leu Ile Thr Gly Arg Leu Gln Ser Leu Gln
305                 310                 315                 320

Thr Tyr Val Thr Gln Gln Leu Ile Arg Ala Ala Glu Ile Arg Ala Ser
                325                 330                 335

Ala Asn Leu Ala Ala Thr Lys Met Ser Glu Cys Val Leu Gly Gln Ser
            340                 345                 350

Lys Arg Val Asp Phe Cys Gly Lys Gly Tyr His Leu Met Ser Phe Pro
            355                 360                 365

Gln Ser Ala Pro His Gly Val Val Phe Leu His Val Thr Tyr Val Pro
            370                 375                 380

Ala Gln Glu Lys Asn Phe Thr Thr Ala Pro Ala Ile Cys His Asp Gly
385                 390                 395                 400

Lys Ala His Phe Pro Arg Glu Gly Val Phe Val Ser Asn Gly Thr His
                405                 410                 415

Trp Phe Val Thr Gln Arg Asn Phe Tyr Glu Pro Gln Ile Ile Thr Thr
            420                 425                 430

Asp Asn Thr Phe Val Ser Gly Asn Cys Asp Val Val Ile Gly Ile Val
            435                 440                 445

Asn Asn Thr Val Tyr Asp Pro Leu Gln Pro Glu Leu Asp Ser Phe Lys
450                 455                 460

Glu Glu Leu Asp Lys Tyr Phe Lys Asn His Thr Ser Pro Asp Val Asp
465                 470                 475                 480

Leu Gly Asp Ile Ser Gly Ile Asn Ala Ser Val Val Asn Ile Gln Lys
                485                 490                 495

Glu Ile Asp Arg Leu Asn Glu Val Ala Lys Asn Leu Asn Glu Ser Leu
            500                 505                 510

Ile Asp Leu Gln Glu Leu Gly Lys Tyr Glu Gln Tyr Ile Lys Trp Pro
            515                 520                 525

<210> SEQ ID NO 4
<211> LENGTH: 534
<212> TYPE: PRT
<213> ORGANISM: Artificial Sequence
<220> FEATURE:
<223> OTHER INFORMATION: Polypeptide

<400> SEQUENCE: 4

Ser Val Ala Ser Gln Ser Ile Ile Ala Tyr Thr Met Ser Leu Gly Ala
1               5                   10                  15

Glu Asn Ser Val Ala Tyr Ser Asn Asn Ser Ile Ala Ile Pro Thr Asn
                20                  25                  30

Phe Thr Ile Ser Val Thr Thr Glu Ile Leu Pro Val Ser Met Thr Lys
```

```
            35                  40                  45
Thr Ser Val Asp Cys Thr Met Tyr Ile Cys Gly Asp Ser Thr Glu Cys
 50                  55                  60

Ser Asn Leu Leu Leu Gln Tyr Gly Ser Phe Cys Thr Gln Leu Asn Arg
 65                  70                  75                  80

Ala Leu Thr Gly Ile Ala Val Glu Gln Asp Lys Asn Thr Gln Glu Val
                 85                  90                  95

Phe Ala Gln Val Lys Gln Ile Tyr Lys Thr Pro Pro Ile Lys Asp Phe
                100                 105                 110

Gly Gly Phe Asn Phe Ser Gln Ile Leu Pro Asp Pro Ser Lys Pro Ser
                115                 120                 125

Lys Arg Ser Phe Ile Glu Asp Leu Leu Phe Asn Lys Val Thr Leu Ala
130                 135                 140

Asp Ala Gly Phe Ile Lys Gln Tyr Gly Asp Cys Leu Gly Asp Ile Ala
145                 150                 155                 160

Ala Arg Asp Leu Ile Cys Ala Gln Lys Phe Asn Gly Leu Thr Val Leu
                165                 170                 175

Pro Pro Leu Leu Thr Asp Glu Met Ile Ala Gln Tyr Thr Ser Ala Leu
                180                 185                 190

Leu Ala Gly Thr Ile Thr Ser Gly Trp Thr Phe Gly Ala Gly Ala Ala
                195                 200                 205

Leu Gln Ile Pro Phe Ala Met Gln Met Ala Tyr Arg Phe Asn Gly Ile
210                 215                 220

Gly Val Thr Gln Asn Val Leu Tyr Glu Asn Gln Lys Leu Ile Ala Asn
225                 230                 235                 240

Gln Phe Asn Ser Ala Ile Gly Lys Ile Gln Asp Ser Leu Ser Ser Thr
                245                 250                 255

Ala Ser Ala Leu Gly Lys Leu Gln Asp Val Val Asn Gln Asn Ala Gln
                260                 265                 270

Ala Leu Asn Thr Leu Val Lys Gln Leu Ser Ser Asn Phe Gly Ala Ile
                275                 280                 285

Ser Ser Val Leu Asn Asp Ile Leu Ser Arg Leu Asp Lys Val Glu Ala
290                 295                 300

Glu Val Gln Ile Asp Arg Leu Ile Thr Gly Arg Leu Gln Ser Leu Gln
305                 310                 315                 320

Thr Tyr Val Thr Gln Gln Leu Ile Arg Ala Ala Glu Ile Arg Ala Ser
                325                 330                 335

Ala Asn Leu Ala Ala Thr Lys Met Ser Glu Cys Val Leu Gly Gln Ser
                340                 345                 350

Lys Arg Val Asp Phe Cys Gly Lys Gly Tyr His Leu Met Ser Phe Pro
                355                 360                 365

Gln Ser Ala Pro His Gly Val Val Phe Leu His Val Thr Tyr Val Pro
                370                 375                 380

Ala Gln Glu Lys Asn Phe Thr Thr Ala Pro Ala Ile Cys His Asp Gly
385                 390                 395                 400

Lys Ala His Phe Pro Arg Glu Gly Val Phe Val Ser Asn Gly Thr His
                405                 410                 415

Trp Phe Val Thr Gln Arg Asn Phe Tyr Glu Pro Gln Ile Ile Thr Thr
                420                 425                 430

Asp Asn Thr Phe Val Ser Gly Asn Cys Asp Val Val Ile Gly Ile Val
                435                 440                 445

Asn Asn Thr Val Tyr Asp Pro Leu Gln Pro Glu Leu Asp Ser Phe Lys
450                 455                 460
```

```
Glu Glu Leu Asp Lys Tyr Phe Lys Asn His Thr Ser Pro Asp Val Asp
465                 470                 475                 480

Leu Gly Asp Ile Ser Gly Ile Asn Ala Ser Val Val Asn Ile Gln Lys
            485                 490                 495

Glu Ile Asp Arg Leu Asn Glu Val Ala Lys Asn Leu Asn Glu Ser Leu
        500                 505                 510

Ile Asp Leu Gln Glu Leu Gly Lys Tyr Glu Gln Tyr Ile Lys Trp Pro
        515                 520                 525

His His His His His His
        530

<210> SEQ ID NO 5
<211> LENGTH: 26
<212> TYPE: PRT
<213> ORGANISM: Artificial Sequence
<220> FEATURE:
<223> OTHER INFORMATION: Polypeptide

<400> SEQUENCE: 5

Lys Arg Arg Trp Lys Lys Asn Phe Ile Ala Val Ser Ala Ala Asn Arg
1               5                   10                  15

Phe Lys Lys Ile Ser Ser Ser Gly Ala Leu
            20                  25

<210> SEQ ID NO 6
<211> LENGTH: 7
<212> TYPE: PRT
<213> ORGANISM: Artificial Sequence
<220> FEATURE:
<223> OTHER INFORMATION: Polypeptide

<400> SEQUENCE: 6

Asp Tyr Lys Asp Asp Asp Asp
1               5

<210> SEQ ID NO 7
<211> LENGTH: 8
<212> TYPE: PRT
<213> ORGANISM: Artificial Sequence
<220> FEATURE:
<223> OTHER INFORMATION: Polypeptide

<400> SEQUENCE: 7

Asp Tyr Lys Asp Asp Asp Asp Lys
1               5

<210> SEQ ID NO 8
<211> LENGTH: 7
<212> TYPE: PRT
<213> ORGANISM: Artificial Sequence
<220> FEATURE:
<223> OTHER INFORMATION: Polypeptide

<400> SEQUENCE: 8

Asp Tyr Lys Asp Asp Asp Lys
1               5

<210> SEQ ID NO 9
<211> LENGTH: 8
<212> TYPE: PRT
<213> ORGANISM: Artificial Sequence
<220> FEATURE:
<223> OTHER INFORMATION: Polypeptide
```

```
<400> SEQUENCE: 9

Trp Ser His Pro Gln Phe Glu Lys
1               5

<210> SEQ ID NO 10
<211> LENGTH: 10
<212> TYPE: PRT
<213> ORGANISM: Artificial Sequence
<220> FEATURE:
<223> OTHER INFORMATION: Polypeptide

<400> SEQUENCE: 10

Glu Gln Lys Leu Ile Ser Glu Glu Asp Leu
1               5                   10

<210> SEQ ID NO 11
<211> LENGTH: 9
<212> TYPE: PRT
<213> ORGANISM: Artificial Sequence
<220> FEATURE:
<223> OTHER INFORMATION: Polypeptide

<400> SEQUENCE: 11

Tyr Pro Tyr Asp Val Pro Asp Tyr Ala
1               5

<210> SEQ ID NO 12
<211> LENGTH: 13
<212> TYPE: PRT
<213> ORGANISM: Artificial Sequence
<220> FEATURE:
<223> OTHER INFORMATION: Polypeptide

<400> SEQUENCE: 12

Ser Arg Leu Glu Glu Glu Leu Arg Arg Arg Leu Thr Glu
1               5                   10

<210> SEQ ID NO 13
<211> LENGTH: 4
<212> TYPE: PRT
<213> ORGANISM: Artificial Sequence
<220> FEATURE:
<223> OTHER INFORMATION: Polypeptide

<400> SEQUENCE: 13

Glu Pro Glu Ala
1

<210> SEQ ID NO 14
<211> LENGTH: 26
<212> TYPE: PRT
<213> ORGANISM: Artificial Sequence
<220> FEATURE:
<223> OTHER INFORMATION: Polypeptide

<400> SEQUENCE: 14

Lys Arg Arg Trp Lys Lys Asn Phe Ile Ala Val Ser Ala Ala Asn Arg
1               5                   10                  15

Phe Lys Lys Ile Ser Ser Ser Gly Ala Leu
            20                  25

<210> SEQ ID NO 15
<211> LENGTH: 13
<212> TYPE: PRT
<213> ORGANISM: Artificial Sequence
<220> FEATURE:
```

-continued

```
<223> OTHER INFORMATION: Polypeptide

<400> SEQUENCE: 15

Gly Ala Pro Val Pro Tyr Pro Asp Pro Leu Glu Pro Arg
1               5                   10

<210> SEQ ID NO 16
<211> LENGTH: 6
<212> TYPE: PRT
<213> ORGANISM: Artificial Sequence
<220> FEATURE:
<223> OTHER INFORMATION: Polypeptide

<400> SEQUENCE: 16

His His His His His His
1               5

<210> SEQ ID NO 17
<211> LENGTH: 15
<212> TYPE: PRT
<213> ORGANISM: Artificial Sequence
<220> FEATURE:
<223> OTHER INFORMATION: Polypeptide

<400> SEQUENCE: 17

Gly Leu Asn Asp Ile Phe Glu Ala Gln Lys Ile Glu Trp His Glu
1               5                   10                  15

<210> SEQ ID NO 18
<211> LENGTH: 6
<212> TYPE: PRT
<213> ORGANISM: Artificial Sequence
<220> FEATURE:
<223> OTHER INFORMATION: Polypeptide

<400> SEQUENCE: 18

Glu Glu Glu Glu Glu Glu
1               5
```

US 11,119,103 B1

SEROLOGICAL ASSAYS FOR SARS-COV-2

SEQUENCE LISTING

This application contains a sequence listing which has been submitted electronically in ASCII format and is hereby incorporated by reference in its entirety (said ASCII copy, created on Jun. 12, 2020, is named "UA20-226 PR (706843)_ST25.txt" and is 16,947 bytes in size).

BACKGROUND

Severe acute respiratory syndrome coronavirus 2 (SARS-CoV-2) is a highly infectious virus leading to the COVID-19 pandemic, affecting millions of people worldwide. SARS-CoV-2 infection can cause a variety of severe symptoms, including cytokine release syndrome, which may lead to death. In order to mitigate the pandemic, it is necessary to implement effective means to screen potentially infected patients, treat said patients, and determine the total number of current and previously infected patients.

Screening potentially infected patients generally relies on a PCR-based test to determine infection status. These tests have been reliable in accurately screening for current, active infections. To determine if individuals have been infected with and recovered from SARS-CoV-2, a reliable serological-based (i.e., antibody-based) test is important. Unfortunately, the existing serological tests have poor accuracy, with high false positive and false negative results. Moreover, the current serological tests lack the ability to accurately predict if a tested patient's anti-SARS-CoV-2 antibodies are neutralizing anti-SARS-CoV-2 antibodies, thereby conferring active immunity. Accordingly, there exists a need for reliable SARS-CoV-2 serological tests that have low false positive and false negative results and that can accurately predict if a patient has neutralizing anti-SARS-CoV-2 antibodies.

SUMMARY

In one aspect, the disclosure provides a test system comprising: a first surface comprising a first antigen comprising an amino acid sequence of at least 50 amino acids in length and less than 300 amino acids in length that has at least 99% identity to the amino acid sequence of the severe acute respiratory syndrome coronavirus 2 (SARS-CoV-2) receptor binding domain (RBD) antigen; and a second surface comprising a second antigen comprising an amino acid sequence of at least 100 amino acids in length and less than 600 amino acids in length that has at least 99% identity to the amino acid sequence of the SARS-CoV-2 S2 antigen, one or more first binding moieties that specifically bind to a constant region of human IgG, one or more second binding moieties that specifically bind to a constant region of human IgA and one or more third binding moieties that specifically bind to a constant region of human IgM.

In an embodiment, the first antigen comprises the amino acid sequence of SARS-CoV-2 RBD antigen.

In an embodiment, the second antigen comprises the amino acid sequence of SARS-CoV-2 S2 antigen.

In an embodiment, the binding moieties are antibodies.

In an embodiment, the first, second and third binding moieties further comprise a detectable moiety.

In an embodiment, the first surface is substantially free from full-length SARS-CoV-2 spike protein.

In an embodiment, the first surface is substantially free from a fragment of full-length SARS-CoV-2 S1 protein greater than 300 amino acids in length or a fragment of full-length SARS-CoV-2 S1 protein that does not comprise the RBD.

In an embodiment, the second surface is substantially free from full-length SARS-CoV-2 spike protein.

In an embodiment, the second surface is substantially free from full-length SARS-CoV-2 S1 protein.

In an embodiment, the detectable moiety is a chromogenic label.

In an embodiment, the chromogenic label comprises horseradish peroxidase (HRP).

In an embodiment, incubation of the first, second or third binding moieties with an HRP substrate produces a colorimetric signal.

In an embodiment, the first surface is contained within a first well and the second surface is contained in a second well.

In another aspect, the disclosure provides a test system comprising: a first well comprising: an immobilized first binding moiety that specifically binds to a constant region of human IgG, an immobilized second binding moiety that specifically binds to a constant region of human IgA and an immobilized third binding moiety that specifically binds to a constant region of human IgM; a first biological sample from a host; and a first antigen comprising an amino acid sequence of at least 50 amino acids in length and less than 300 amino acids in length that has at least 99% identity to the amino acid sequence of the severe acute respiratory syndrome coronavirus 2 (SARS-CoV-2) receptor binding domain (RBD) antigen, wherein the first antigen comprises a detectable moiety; and a second well comprising: an immobilized first binding moiety that specifically binds to a constant region of human IgG, an immobilized second binding moiety that specifically binds to a constant region of human IgA and an immobilized third binding moiety that specifically binds to a constant region of human IgM; a second biological sample from the host; and a second antigen an amino acid sequence of at least 100 amino acids in length and less than 600 amino acids in length that has at least 99% identity to the amino acid sequence of the SARS-CoV-2 S2 antigen, wherein the second antigen comprises a detectable moiety.

In one aspect, the disclosure provides a kit, comprising the test system recited above, comprising: the first antigen; the second antigen; and the first binding moiety, the second binding moiety, and the third binding moiety, in separate containers.

In one aspect, the disclosure provides a method for detecting the presence of host antigen-specific antibodies that specifically bind SARS-CoV-2, the method comprising the steps of: 1) exposing a first biological sample from the host to a first surface comprising a first antigen comprising an amino acid sequence of at least 50 amino acids in length and less than 300 amino acids in length that has at least 99% identity to the amino acid sequence of the severe acute respiratory syndrome coronavirus 2 (SARS-CoV-2) receptor binding domain (RBD) antigen; 2) incubating the first surface with a first binding moiety that specifically binds to a constant region of human IgG, a second binding moiety that specifically binds to a constant region of human IgA and a third binding moiety that specifically binds to a constant region of human IgM; 3) detecting binding of one or more of the first, second and third binding moieties at the first surface to host antigen-specific antibodies, which generates a first signal; 4) exposing a second biological sample from the host to a second surface comprising a second antigen an amino acid sequence of at least 100 amino acids in length and less than 600 amino acids in length that has at least 99% identity to the amino acid sequence of the SARS-CoV-2 S2 antigen; 5) incubating the first surface with a fourth binding moiety that specifically binds to a constant region of human IgG, a fifth binding moiety that specifically binds to a constant region of human IgA and a sixth binding moiety that specifically binds to a constant region of human IgM; and 6) detecting binding of one or more of the fourth, fifth and sixth binding moieties at the second surface to host antigen-specific antibodies, which generates a second signal, thereby detecting the presence of host antigen-specific antibodies that specifically bind SARS-CoV-2.

In an embodiment, the first antigen comprises the amino acid sequence of SARS-CoV-2 RBD antigen.

In an embodiment, the second antigen comprises the amino acid sequence of SARS-CoV-2 S2 antigen.

In an embodiment, the binding moieties are antibodies.

In an embodiment, the first, second, third, fourth, fifth and sixth binding moieties further comprise a detectable moiety.

In an embodiment, the first surface is substantially free from full-length SARS-CoV-2 spike protein.

In an embodiment, the first surface is substantially free from a fragment of full-length SARS-CoV-2 S1 protein greater than 300 amino acids in length or a fragment of full-length SARS-CoV-2 S1 protein that does not comprise the RBD.

In an embodiment, the second surface is substantially free from full-length SARS-CoV-2 spike protein.

In an embodiment, the second surface is substantially free from full-length SARS-CoV-2 S1 protein.

In an embodiment, the first binding moiety is the same as the fourth binding moiety, the second binding moiety is the same as the fifth binding moiety and/or the third binding moiety is the same as the sixth binding moiety.

In an embodiment, the biological sample is selected from the group consisting of serum, blood, plasma, sputum, urine, semen, mucous, sweat and tears.

In an embodiment, the detectable moiety is a chromogenic label.

In an embodiment, the chromogenic label comprises horseradish peroxidase (HRP).

In an embodiment, incubation of the first, second and third binding moieties with an HRP substrate produces a colorimetric signal.

In an embodiment, a first signal value that is at least five standard deviations above a negative control sample indicates a first positive result; a first signal value that is at least three standard deviations but less than five standard deviations above a negative control sample indicates a first indeterminate result; a first signal value that is less than three standard deviations above a negative control sample indicates a first negative result; a second signal value that is at least five standard deviations above a negative control sample indicates a second positive result; a second signal value that is at least three standard deviations but less than five standard deviations above a negative control sample indicates a second indeterminate result; and a second signal value that is less than three standard deviations above a negative control sample indicates a second negative result.

In an embodiment, a first positive result and a second positive result indicates the presence of host antigen-specific antibodies.

In an embodiment, a first positive result and a second indeterminate result indicates the presence of host antigen-specific antibodies.

In an embodiment, a first positive result and a second negative result indicates an absence of host antigen-specific antibodies.

In an embodiment, a first indeterminate result and a second negative result indicates an absence of host antigen-specific antibodies.

In an embodiment, the host antigen-specific antibodies are neutralizing host antigen-specific antibodies that specifically bind SARS-CoV-2.

In an embodiment, if there is no first positive result, steps 4-6 are not performed.

BRIEF DESCRIPTION OF THE DRAWINGS

FIG. 1 is a graphic representation of steps of the assay of the disclosure.

FIG. 2 is a graphic representation of a correlation of absorbance readings between the CLAIROStar and Synergy plate readers.

FIG. 3 is a graphic representation of the average absorbance measurements ($OD_{450nm}$) compared between different technicians (Tech 1 vs. Tech 2) and different days (plate 1 vs plate 2).

FIG. 4 is a graphic representation of ELISA signals for 30 samples collected from patients prior to the COVID-19 outbreak (left of the center), and 28 samples from patients that have tested positive for COVID-19 with a molecular test (right of center). The black circles and error bar show the average and standard deviation for each patient sample from the four plates. The dark blue, light blue, dark green and light green diamonds show the raw data from each plate (blue technician 1, green technician 2). All data is normalized by subtracting the average negative control signal from the same plate. The orange line shows the three-standard deviation threshold using a standard deviation of $1.5\times10^{-2}$ used as the maximum absorbance to call negative samples. The red line is the 5-standard deviation threshold above which samples are called positive. In between these thresholds, samples are considered indeterminate.

FIG. 5 is a graphic representation of the comparison of iterative run results (where the same plate was read every 15 minutes for 10 hours to assess changes in signal (absorbance over time).

FIG. 6 is a graphic representation of the average $OD_{450nm}$ values (across multiple iterations) for the original validation study positive (n=30) and negative (n=32) specimens plus 320 additional negative specimens to assess cross-reactivity. Re-evaluated thresholds for positive (≥0.389) and negative (≤0.120) interpretation imposed on graph.

FIG. 7 is a graphic representation of the results of neutralization assay performance of the validated "SARS-CoV-2 ELISA pan-Ig Antibody Test" performed in dilution series of 100, 75, 50 and 25%. The graph truncated to 82 specimens with $OD_{450nm}$ reading at 0.15 or above.

FIG. 8 is a graphic representation of the results of the validation sample set OD values RBD vs. S2.

FIG. 9 is a graphic representation of the results of the combined validation and cross-reactivity panel OD data for S2.

DETAILED DESCRIPTION

Severe acute respiratory syndrome coronavirus 2 (SARS-CoV-2) is enveloped, non-segmented positive-sense RNA virus with virions that are spherical with diameters of approximately 125 nm (Barcena M et al., PNAS, 2009; 106(2):582-587; Neuman et al., J Virol. 2006; 80(16):7918-

7928). Like other coronaviruses, SARS-CoV-2 particles contain four main structural proteins. These are the spike (S), membrane (M), envelope (E), and nucleocapsid (N) proteins. The S protein (~150 kDa) forms homotrimers to make up the distinctive spike structure on the surface of the virus (Beniac et al., Nat Struct Mol Biol., 2006; 13(8):751-752; Delmas et al., J Virol. 1990; 64(11):5367-5375). The trimeric S glycoprotein is a class I fusion protein (Bosch et al., J Virol. 2003; 77(16):8801-8811) and mediates attachment to the host receptor (Collins et al., Virology. 1982; 119(2):358-371). In most, but not all, coronaviruses, S is cleaved by a host cell furin-like protease into two separate polypeptides noted S1 and S2 (Abraham et al., Virology. 1990; 176(1):296-301; Luytjes et al., Virology. 1987; 161(2):479-487). S contains the large receptor binding domain (RBD) of the S protein while S2 forms the stalk of the spike molecule (De Groot et al., J Mol Biol. 1987, 196(4):963-966).

The disclosure provides an antibody based test to show a specific immune response in a human subject to SARS-CoV-2 infection. In some embodiments, the test comprises providing a first biological sample from a human subject and exposing that sample to an immobilized SARS-CoV-2 RBD antigen. In some embodiments, after washing away unbound sample, the immobilized antigen is exposed to one or more types of secondary antibody that specifically bind to any IgG, IgA, and/or IgM antibodies from the sample that have specifically bound to the immobilized SARS-CoV-2 RBD antigen. In some embodiments, if specific binding of antibodies from the subject to immobilized SARS-CoV-2 RBD antigen is found, a second biological sample from the same human subject is exposed to an immobilized SARS-CoV-2 S2 antigen. In some embodiments, after washing away unbound sample, the immobilized antigen is exposed to secondary antibody that specifically binds to any IgG, IgA, and/or IgM antibodies from the sample that have specifically bound to the immobilized SARS-CoV-2 S2 antigen. In some embodiments, if specific binding of antibodies from the subject to immobilized SARS-CoV-2 S2 antigen is found the subject is considered positive for having specific antibodies for SARS-CoV-2. In some embodiments, this would indicate that the subject has some degree of immunity to SARS-CoV-2. The disclosure provides various systems, kits and methods of finding this indication, described below.

Definitions

Unless otherwise stated, sequence identity/similarity values provided herein refer to the value obtained using the BLAST 2.0 suite of programs using default parameters (Altschul, et al., (1997) Nucleic Acids Res. 25:3389-402).

As those of ordinary skill in the art will understand, BLAST searches assume that proteins can be modeled as random sequences. However, many real proteins comprise regions of nonrandom sequences, which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, (1993) Comput. Chem. 17:149-63) and XNU (Claverie and States, (1993) Comput. Chem. 17:191-201) low-complexity filters can be employed alone or in combination.

As used herein, "sequence identity" or "identity" in the context of two nucleic acid or polypeptide sequences includes reference to the residues in the two sequences, which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Sequences, which differ by such conservative substitutions, are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, (1988) Computer Applic. Biol. Sci. 4:11-17, e.g., as implemented in the program PC/GENE (Intelligenetics, Mountain View, Calif., USA).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" or "substantially identical" of polynucleotide sequences means that a polynucleotide comprises a sequence that has between 50-100% sequence identity, preferably at least 50% sequence identity, preferably at least 60% sequence identity, preferably at least 70%, more preferably at least 80%, more preferably at least 90% and most preferably at least 95%, compared to a reference sequence using one of the alignment programs described using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of between 75-100%. In some embodiments, identity of amino acid sequences is at least 75%, 80%, 85%, 90%, 91%, 92%, 93%, 94%, 95%, 96%, 97%, 98% or 99%.

The term "amino acid" refers to naturally occurring and synthetic amino acids, as well as amino acid analogs and amino acid mimetics that function in a manner similar to the naturally occurring amino acids, and isomers thereof. Naturally occurring amino acids are those encoded by the genetic code, as well as those amino acids that are later modified, e.g., hydroxyproline, carboxyglutamate, 0-phosphoserine, and isomers thereof. The term "amino acid analogs" refers to compounds that have the same basic chemical structure as a naturally occurring amino acid, i.e., a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. The term "amino acid mimetics" refers to chemical compounds that have a structure that is different from the general chemical structure of an amino acid, but that functions in a manner similar to a naturally occurring amino acid. Amino acids may be referred to herein by either their commonly known three letter symbols or by the one-letter symbols recommended by the IUPAC-IUB Biochemical Nomenclature Commission.

The term "non-natural amino acid" as used herein refers to an amino acid that is different from the twenty naturally occurring amino acids (alanine, arginine, glycine, asparagine, aspartic acid, cysteine, glutamine, glutamic acid, serine, threonine, histidine, lysine, methionine, proline, valine, isoleucine, leucine, tyrosine, tryptophan, phenylalanine) in its side chain functionality. The non-natural amino acid can be a close analog of one of the twenty natural amino acids, or it can introduce a completely new functionality and chemistry, as long as the hydrophobicity of the non-natural amino acid is either equivalent to or greater than that of the natural amino acid. The non-natural amino acid can either replace an existing amino acid in a protein (substitution), or be an addition to the wild type sequence (insertion). The incorporation of non-natural amino acids can be accomplished by known chemical methods including solid-phase peptide synthesis or native chemical ligation, or by biological methods.

As used herein, the term "severe acute respiratory syndrome coronavirus 2 receptor binding domain antigen" or "severe acute respiratory syndrome coronavirus 2 RBD antigen" or "SARS-Cov-2 RBD antigen" or RBD antigen" refers to a portion of the receptor binding domain of the SARS-CoV-2 spike protein. The RBD is represented by the amino acid sequence recited below: MFVFLVLLPLVSSQRVQPTESIVRFPNITNLCPF-GEVFNATRFASVYAWNRKRISNCVAD YSVLYNSASF-STFKCYGVSPTKLNDLCFTNVYADSFVIR-GDEVRQIAPGQTGKIADYNY KLPDDFTGCVIAWNSNNLDSKVGGNYNYLYRL-FRKSNLKPFERDISTEIYQAGSTPCNG VEGFN-CYFPLQSYGFQPTNGVGYQPYRVVVLSFELL-HAPATVCGPKKSTNLVKNKCVN FGLNDIFEAQKIEWHE (SEQ ID NO: 1)

In certain embodiments, the RBD amino acid sequence can be modified with a purification tag to facilitate purification of recombinantly expressed RBD. Non-limiting examples of purification tags include: polyhistidine-tag ($H_n$ where n is 2-10), chitin binding protein (CBP) (KRRWK-KNFIAVSAANRFKKISSSGAL; SEQ ID NO: 5), FLAG tag (DYKDDDD; SEQ ID NO: 6, or DYKDDDDK; SEQ ID NO: 7, or DYKDDDK; SEQ ID NO: 8), glutathione-S-transferase (GST), maltose binding protein (MBP), Strep-tag (W SHPQFEK; SEQ ID NO: 9), Myc-tag (EQKLI-SEEDL; SEQ ID NO: 10), hemagglutinin-tag (HA-tag) (YPYDVPDYA; SEQ ID NO: 11), ALFA-tag, (SR-LEEELRRRLTE; SEQ ID NO: 12), Avi-tag, (GLNDIFEA-QKIEWHE; SEQ ID NO: 17), C-tag (EPEA; SEQ ID NO: 13), Calmodulin-tag (KRRWKKNFIAVSAANRFKKISSS-GAL; SEQ ID NO: 14), polyglutamate tag (EEEEEE; SEQ ID NO: 18), and E-tag (GAPVPYPDPLEPR; SEQ ID NO: 15). In certain embodiments, the RBD amino acid sequence further comprises a polyhistidine tag comprising the amino acid sequence of HHHHHH (SEQ ID NO: 16).

In certain embodiments, the RBD is represented by the amino acid sequence recited below: MFVFLVLLPLVSSQRVQPTESIVRFPNITNLCPF-GEVFNATRFASVYAWNRKRISNCVAD YSVLYNSASF-STFKCYGVSPTKLNDLCFTNVYADSFVIR-GDEVRQIAPGQTGKIADYNY KLPDDFTGCVIAWNSNNLDSKVGGNYNYLYRL-FRKSNLKPFERDISTEIYQAGSTPCNG VEGFN-CYFPLQSYGFQPTNGVGYQPYRVVVLSFELL-HAPATVCGPKKSTNLVKNKCVN FGLNDIFEAQKIEWHEHHHHHH (SEQ ID NO: 2).

In certain embodiments, the purification tag is present at one or both of the N terminus or C terminus of the RBD amino acid sequence. In certain embodiments, the purification tag is present at the N terminus of the RBD amino acid sequence. In certain embodiments, the purification tag is present at the C terminus of the RBD amino acid sequence.

In certain embodiments, the RBD antigen has at least 95%, at least 96%, at least 97%, at least 98%, at least 99%, or 100% identity to the RBD sequence of SEQ ID NO: 1.

In certain embodiments, the RBD antigen is the first antigen in a test system of the invention. In certain embodiments, the first antigen comprises an amino acid sequence of at least 50 amino acids in length and less than 300 amino acids in length that has at least 99% identity to the amino acid sequence of the RBD antigen. In certain embodiments, the first antigen comprises an amino acid sequence of at least 50, at least 60, at least 70, at least 80, at least 90, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or 300 amino acids in length of the amino acid sequence of the RBD antigen. In certain embodiments, the first antigen comprises an amino acid sequence of less than 300, less than 290, less than 280, less than 270, less than 260, less than 250, less than 240, less than 230, less than 220, less than 210, less than 200, less than 190, less than 180, less than 170, less than 160, less than 150, less than 140, less than 130, less than 120, less than 110, less than 100, less than 90, less than 80, less than 70, less than 60, or 50 amino acids in length of the amino acid sequence of the RBD antigen. In certain embodiments, the first antigen comprises an amino acid sequence of between 200 amino acids and 300 amino acids in length of the amino acid sequence of the RBD antigen. In certain embodiments, the first antigen comprises at least 95%, at least 96%, at least 97%, at least 98%, at least 99%, or 100% identity to the amino acid sequence of the RBD antigen.

As used herein, the term "severe acute respiratory syndrome coronavirus 2 S2 antigen" or "SARS-Cov-2 S2 antigen" or S2 antigen" refers to a portion of the S2 domain of the SARS-CoV-2 spike protein. The S2 domain is represented by the amino acid sequence recited below: SVASQSIIAYTMSLGAENSVAYSNNSI-AIPTNFTISVTTEILPVSMTKTSVDCTMYICGDST ECSNLLLQYGSFCTQLNRALTGIA-VEQDKNTQEVFAQVKQIYKTPPIKDFGGFNFSQILP DPSKPSKRSFIEDLLFNKVTLADAGFIKQYGDCLGDI-AARDLICAQKFNGLTVLPPLLTDE MIAQYTSAL-LAGTITSGWTFGAGAALQIPFAMQMAYRFN-GIGVTQNVLYENQKLIANQF NSAIGKIQDSLSSTASALGKLQDVVNQNAQAL-NTLVKQLSSNFGAISSVLNDILSRLDKV EAEVQIDRLITGRLQSLQTYVTQQLIRAAEIRASAN- LAATKMSECVLGQSKRVDFCGKG
YHLMSFPQSAPHGVVFLHVTYVPAQEKNFTTAPA-
ICHDGKAHFPREGVFVSNGTHWFV
TQRNFYEPQIITTDNTFVSGNCDVVI-
GIVNNTVYDPLQPELDSFKEELDKYFKNHTSPDV
DLGDISGINASVVNIQKEIDRLNEVAKNLNESL-
IDLQELGKYEQYIKWP (SEQ ID NO: 3)

In certain embodiments, the S2 domain amino acid sequence can be modified with a purification tag to facilitate purification of recombinantly expressed S2. Non-limiting examples of purification tags include: polyhistidine-tag ($H_n$ where n is 2-10), chitin binding protein (CBP) (KRRWK-KNFIAVSAANRFKKISSSGAL; SEQ ID NO: 5), FLAG tag (DYKDDDD; SEQ ID NO: 6, or DYKDDDDK; SEQ ID NO: 7, or DYKDDDK; SEQ ID NO: 8), glutathione-S-transferase (GST), maltose binding protein (MBP), Strep-tag (W SHPQFEK; SEQ ID NO: 9), Myc-tag (EQKLI-SEEDL; SEQ ID NO: 10), hemagglutinin-tag (HA-tag) (YPYDVPDYA; SEQ ID NO: 11), ALFA-tag, (SR-LEEELRRRLTE; SEQ ID NO: 12), Avi-tag, (GLNDIFEA-QKIEWHE; SEQ ID NO: 17), C-tag (EPEA; SEQ ID NO: 13), Calmodulin-tag (KRRWKKNFIAVSAANRFKKISSS-GAL; SEQ ID NO: 14), polyglutamate tag (EEEEEE; SEQ ID NO: 18), and E-tag (GAPVPYPDPLEPR; SEQ ID NO: 15). In certain embodiments, the RBD amino acid sequence further comprises a polyhistidine tag comprising the amino acid sequence of HHHHHH (SEQ ID NO: 16).

In certain embodiments, the S2 domain is represented by the amino acid sequence recited below: SVASQSIIAY-TMSLGAENSVAYSNNSIAIPTNFTISVTTEIL-PVSMTKTSVDCTMYICGDST ECSNLLLQYGSFCTQLNRALTGIA-VEQDKNTQEVFAQVKQIYKTPPIKDFGGFNFSQILP DPSKPSKRSFIEDLLFNKVTLADAGFIKQYGDCLGDI-AARDLICAQKFNGLTVLPPLLTDE MIAQYTSAL-LAGTITSGWTFGAGAALQIPFAMQMAYRFN-GIGVTQNVLYENQKLIANQF NSAIGKIQDSLSSTASALGKLQDVVNQNAQAL-NTLVKQLSSNFGAISSVLNDILSRLDKV EAEVQIDRLITGRLQSLQTYVTQQLIRAAEIRASAN-LAATKMSECVLGQSKRVDFCGKG YHLMSFPQSAPHGVVFLHVTYVPAQEKNFTTAPA-ICHDGKAHFPREGVFVSNGTHWFV TQRNFYEPQIITTDNTFVSGNCDVVI-GIVNNTVYDPLQPELDSFKEELDKYFKNHTSPDV DLGDISGINASVVNIQKEIDRLNEVAKNLNESL-IDLQELGKYEQYIKWPHHHHHH (SEQ ID NO: 4)

In certain embodiments, the purification tag is present at one or both of the N terminus or C terminus of the S2 domain amino acid sequence. In certain embodiments, the purification tag is present at the N terminus of the S2 domain amino acid sequence. In certain embodiments, the purification tag is present at the C terminus of the S2 domain amino acid sequence.

In certain embodiments, the S2 antigen has at least 95%, at least 96%, at least 97%, at least 98%, at least 99%, or 100% identity to the S2 sequence of SEQ ID NO: 3.

In certain embodiments, the S2 antigen is the second antigen in a test system of the invention. In certain embodiments, the second antigen comprises an amino acid sequence of at least 100 amino acids in length and less than 600 amino acids in length that has at least 99% identity to the amino acid sequence of the S2 antigen. In certain embodiments, the second antigen comprises an amino acid sequence of at least about 100, at least about 150, at least about 200, at least about 250, at least about 300, at least about 350, at least about 400, at least about 450, at least about 500, at least about 550, or about 600 amino acids in length of the amino acid sequence of the S2 antigen. In certain embodiments, the second antigen comprises an amino acid sequence of less than about 600, less than about 550, less than about 500, less than about 450, less than about 400, less than about 350, less than about 300, less than about 250, less than about 200, less than about 150, or about 100 amino acids in length of the amino acid sequence of the S2 antigen. In certain embodiments, the second antigen comprises at least 95%, at least 96%, at least 97%, at least 98%, at least 99%, or 100% identity to the amino acid sequence of the S2 antigen.

As used herein, the term "surface" refers to any surface which can immobilize a polypeptide (e.g., a RBD antigen and an S2 antigen). In certain embodiments, the surface comprises a polystyrene surface. In certain embodiments, the polystyrene surface is contained in a well, such as a well of a microtiter plate. The microtiter plate can have 96 wells or 384 wells.

In certain embodiments, the proteins of the disclosure (e.g., the RBD antigen and the S2 antigen) are immobilized on a surface through absorption. In certain embodiments, the proteins of the disclosure (e.g., the RBD antigen and the S2 antigen) are immobilized on a surface through chemical crosslinking. In certain embodiments, the proteins of the disclosure (e.g., the RBD antigen and the S2 antigen) are immobilized on a surface through a magnetic interaction.

As used herein, the term "binding moiety" refers to an agent that specifically binds to a specific target. Non-limiting examples of binding moieties include antibodies and fragments thereof, aptamers, fibronectin domains, affibodies, affilins, affimers, affitins, alphabodies, anticalins, avimers, DARPins, Fynomers, and monobodies.

As used herein, the term "antibody" or "antigen binding protein" refers to an immunoglobulin molecule that specifically binds to, or is immunologically reactive with an antigen or epitope, and includes both polyclonal and monoclonal antibodies, as well as functional antibody fragments, including but not limited to fragment antigen-binding (Fab) fragments, F(ab')2 fragments, Fab' fragments, Fv fragments, recombinant IgG (rIgG) fragments, single chain variable fragments (scFv) and single domain antibodies (e.g., sdAb, sdFv, nanobody) fragments. The term "antibody" includes genetically engineered or otherwise modified forms of immunoglobulins, such as intrabodies, peptibodies, chimeric antibodies, fully human antibodies, humanized antibodies, heteroconjugate antibodies (e.g., bispecific antibodies, diabodies, triabodies, tetrabodies, tandem di-scFv, tandem tri-scFv) and the like. Unless otherwise stated, the term "antibody" should be understood to encompass functional antibody fragments thereof. Moreover, the term "antibody" includes all of the different human isotypes of antibodies, IgA, IgD, IgE, IgG, and IgM.

As used herein, the term "antigen" refers to a biological molecule that promotes an immune response. In some embodiments, an antigen is a viral protein that promotes an immune response. In some embodiments, an antigen is a protein from SARS-CoV-2. In some embodiments is a fragment of the SARS-CoV-2 spike protein. In some embodiments, an antigen is an S, S2 or RBD domain of the SARS-CoV-2 spike protein.

The terms "specific binding," "selective binding," "selectively binds," or "specifically binds" as used herein refer to binding of a moiety to an epitope on a predetermined antigen. Typically, the binding moiety binds with an affinity ($k_D$) of approximately less than $10^{-7}$ M, such as approximately less than $10^{-8}$ M, $10^{-9}$ M or $10^{-10}$ M or even lower.

The term "$K_D$" as used herein refers to the dissociation equilibrium constant of a particular binding moiety-antigen interaction. Typically, the binding moieties of the invention bind to the constant regions of IgG, IgA and/or IgM with a dissociation equilibrium constant ($K_D$) of less than approximately $10^{-6}$ M, such as less than approximately $10^{-7}$ M, $10^{-8}$ M, $10^{-9}$ M or $10^{-10}$ M or even lower, for example, as determined using surface plasmon resonance (SPR) technology in a Biacore instrument using the antigen as the ligand and the binding moiety as the analyte, and binds to the predetermined antigen with an affinity corresponding to a $K_D$ that is at least ten-fold lower, such as at least 100 fold lower, for instance at least 1000 fold lower, such as at least 10,000 fold lower, for instance at least 100,000 fold lower than its affinity for binding to a non-specific antigen (e.g., BSA, casein) other than the predetermined antigen or a closely-related antigen. The amount with which the affinity is lower is dependent on the $K_D$ of the binding moiety, so that when the $K_D$ of the binding moiety is very low (that is, the binding moiety is highly specific), then the amount with which the affinity for the antigen is lower than the affinity for a non-specific antigen may be at least 10,000 fold.

The term "$k_d$" ($sec^{-1}$) as used herein refers to the dissociation rate constant of a particular binding moiety-antigen interaction. Said value is also referred to as the $k_{off}$ value.

The term "$k_a$" ($M^{-1} \times sec^{-1}$) as used herein refers to the association rate constant of a particular binding moiety-antigen interaction.

The term "$K_D$" (M) as used herein refers to the dissociation equilibrium constant of a particular binding moiety-antigen interaction.

The term "$K_A$" ($M^{-1}$) as used herein refers to the association equilibrium constant of a particular binding moiety-antigen interaction and is obtained by dividing the $k_a$ by the $k_d$.

Test Systems

In one aspect, the disclosure provides a test system comprising: a first surface comprising a first antigen comprising an amino acid sequence of at least 50 amino acids in length and less than 100 amino acids in length that has at least 99% identity to the amino acid sequence of the severe acute respiratory syndrome coronavirus 2 (SARS-CoV-2) receptor binding domain (RBD) antigen; and a second surface comprising a second antigen comprising an amino acid sequence of at least 100 amino acids in length and less than 600 amino acids in length that has at least 99% identity to the amino acid sequence of the SARS-CoV-2 S2 antigen, one or more first binding moieties that specifically bind to a constant region of human IgG, one or more second binding moieties that specifically bind to a constant region of human IgA and one or more third binding moieties that specifically bind to a constant region of human IgM.

As used herein, human "IgG" refers to human immunoglobulin G and includes all 4 subtypes (IgG1, IgG2, IgG3, and IgG4).

As used herein, human "IgA" refers to human immunoglobulin A and includes both subtypes (IgA1 and IgA2). IgA comes in a serum form and a secretory form. The secretory form is referred to as secretory IgA or sIgA. IgA can exist as a multimer, such as a dimer, a trimer, and a tetramer.

As used herein, human "IgM" refers to human immunoglobulin M. The IgM heavy chain includes four distinct constant regions (Cμ1, Cμ2, Cμ3, Cμ4). IgM can exist as a multimer, and in particular a pentamer. IgM is often the first antibody type produced in response to an initial exposure to an antigen (e.g., a SARS-CoV-2 antigen).

As used herein, the terms "constant region" and "constant domain" are interchangeable and are common in the art. The constant region is an antibody portion, e.g., a carboxyl terminal portion of a light and/or heavy chain which is not directly involved in binding of an antibody to antigen but which can exhibit various effector functions, such as interaction with an Fc receptor (e.g., Fc gamma receptor). The constant region of an immunoglobulin molecule generally has a more conserved amino acid sequence relative to an immunoglobulin variable domain.

As used herein, the term "heavy chain" when used in reference to an antibody can refer to any distinct type, e.g., alpha (α), delta (δ), epsilon (ε), gamma (γ), and mu (μ), based on the amino acid sequence of the constant domain, which give rise to IgA, IgD, IgE, IgG, and IgM isotypes of antibodies, respectively, including subtypes of IgG, e.g., IgG1, IgG2, IgG3, and IgG4.

As used herein, the term "light chain" when used in reference to an antibody can refer to any distinct type, e.g., kappa (κ) or lambda (λ) based on the amino acid sequence of the constant domains. Light chain amino acid sequences are well known in the art. In specific embodiments, the light chain is a human light chain.

The numbering of the amino acids in the heavy and light immunoglobulin chains run from the N-terminus at the forked ends of the Y configuration to the C-terminus at the bottom of each chain. Different numbering schemes are used to define the constant domains of the immunoglobulin heavy and light chains. In accordance with the EU numbering scheme, the heavy chain constant domains of an IgG molecule are identified as follows: CH1—amino acid residues 118-215; CH2—amino acid residues 231-340; CH3—amino acid residues 341-446. In accordance with the Kabat numbering scheme, the heavy chain constant domains of an IgG molecule are identified as follows: CH1—amino acid residues 114-223; CH2—amino acid residues 244-360; CH3—amino acid residues 361-477. The "Fc domain" or "Fc region" typically defines the portion of the constant region of a heavy chain including the CH2 and CH3 domains. The Fc region may also include some residues from the hinge region. The "hinge region" includes the portion of a heavy chain molecule that joins the CH1 domain to the CH2 domain. This hinge region comprises approximately 25 residues and is flexible, thus allowing the two N-terminal antigen binding regions to move independently. Hinge regions can be subdivided into three distinct domains: upper, middle, and lower hinge domains (Roux K. H. et al. J. Immunol. 161:4083-90 1998).

In some embodiments, the SARS-CoV-2 RBD antigen comprises or consists of an amino acid sequence of at least 50 amino acids in length and less than 300 amino acids in length that has at least 99% identity to the amino acid sequence of SEQ ID NO:1. In some embodiments, the first antigen comprises the amino acid sequence of SARS-CoV-2 RBD antigen. In certain embodiments of the test system, the first antigen consists of the amino acid sequence of SARS-CoV-2 RBD antigen.

In some embodiments, the SARS-CoV-2 S2 antigen comprises or consists of an amino acid sequence of at least 100 amino acids in length and less than 600 amino acids in length that has at least 99% identity to SEQ ID NO:3. In certain embodiments of the test system, the second antigen comprises the amino acid sequence of SARS-CoV-2 S2 antigen. In certain embodiments of the test system, the second antigen consists of the amino acid sequence of SARS-CoV-2 S2 antigen.

In certain embodiments of the test system, the binding moieties are antibodies or fragments thereof. In certain embodiments of the test system, the first, second and/or third binding moieties further comprise a detectable moiety. In certain embodiments, the detectable moiety is a chromogenic label. In certain embodiments of the test system, the chromogenic label comprises horseradish peroxidase (HRP). In some embodiments, the HRP substrate is selected from the group consisting of 3,3',5,5'-Tetramethylbenzidine (TMB), o-Phenylenediamine dihydrochloride (OPD), and 2,2'-Azinobis [3-ethylbenzothiazoline-6-sulfonic acid]-diammonium salt (ABTS).

In some embodiments, the chromogenic label comprises Alkaline Phosphatase (Alk-phos). In some embodiments, the Alk-phos substrate comprises para-nitrophenylphosphate (pNPP).

In some embodiments, the chromogenic label comprises β-Galactosidase (β-gal). In some embodiments, the β-gal substrate comprises a β-galactoside, such as ortho-nitrophenyl-β-galactoside (ONPG) or 5-bromo-4-chloro-3-indolyl-β-d-galactopyranoside (X-gal).

In some embodiments, the chromogenic label comprises a urease. In some embodiments, the urease substrate comprises Urea bromocresol.

In some embodiments, detectable moiety is a fluorescent label. In some embodiments, a fluorescently labeled detectable moiety is detected and quantified by, for example, measuring the increased fluorescence polarization arising from the complex-bound peptide relative to that of the free peptide.

In some embodiments, the antibody is labeled with a detectable moiety selected from the group consisting of biotin, copper-DOTA, biotin-PEG3, aminooxyacetate, $^{19}$FB, $^{18}$FB and FITC-PEG3. In other embodiments, the binding moiety is labeled with the detectable moiety consisting of $^{64}$Cu DOTA, $^{68}$Ga DOTA, $^{18}$F, $^{64}$Cu, $^{68}$Ga $^{89}$Zr, $^{124}$I, $^{86}$Y, $^{94m}$Tc, $^{110m}$In $^{11}$C and $^{76}$Br.

In some embodiments, SARS-CoV-2 antigens are immobilized on a solid substrate such as a chromatographic support or other matrix material, then the immobilized antigens can be contacted with biological sample under conditions suitable for formation of an antigen/antibody complex. The non-binding portion of the biological sample can be removed and the complex can be detected, for example, using binding moieties that specifically bind to IgG, IgA and/or IgM.

In some embodiments, the test system comprises an immunoassay selected from a Western blot, pull-down assay, dot blot, and ELISA. In some embodiments, a sandwich-type "ELISA" assay can be used, wherein SARS-CoV-2 RBD antigen is immobilized on a surface of a first plastic tube or well and SARS-CoV-2 S2 antigen is immobilized on a surface of a second plastic tube or well. In some embodiments, the first well is contacted with a biological sample from a human subject and then binding moieties that specifically bind to the constant regions of human IgG, IgA and/or IgM are introduced. In some embodiments, specific association of the binding moieties with the SARS-CoV-2 RBD antigen are detected. In some embodiments, if the binding moieties are associated with the SARS-CoV-2 S2 antigen, then the second well is contacted with a biological sample from the same human subject and then binding moieties that specifically bind to the constant regions of human IgG, IgA and/or IgM are introduced. In some embodiments, specific association of the binding moieties with the SARS-CoV-2 S2 antigen are detected.

In certain embodiments of the test system, the first surface is substantially free from full-length SARS-CoV-2 spike protein. As used herein, the term "substantially free" refers to an amount of a molecule that does not affect the rate of positive, intermediate and negative results produced by the test system or methods of using the test system described herein. In some embodiments, the term "substantially free" refers to the presence of a contaminant at less than about 5%, less than about 4%, less than about 3%, less than about 2%, or less then about 1% of a total composition. In certain embodiments of the test system, the first surface comprises less than about 5%, less than about 4%, less than about 3%, less than about 2%, or less then about 1% of immobilized full-length SARS-CoV-2 spike protein relative to immobilized SARS-CoV-2 RBD antigen. In some embodiments, the first surface is free of detectable full-length SARS-CoV-2 spike protein. In some embodiments, the first surface is free of full-length SARS-CoV-2 spike protein.

In certain embodiments of the test system, the first surface is substantially free from a fragment of full-length SARS-CoV-2 S1 protein greater than 300 amino acids in length or a fragment of full-length SARS-CoV-2 S1 protein that does not comprise the RBD. In certain embodiments of the test system, the first surface comprises less than about 5%, less than about 4%, less than about 3%, less than about 2%, or less then about 1% of an immobilized fragment of full-length SARS-CoV-2 S protein greater than 300 amino acids in length or a fragment of full-length SARS-CoV-2 S1 protein that does not comprise the RBD, relative to immobilized SARS-CoV-2 RBD antigen. In some embodiments, the first surface is free of a detectable fragment of full-length SARS-CoV-2 S protein greater than 300 amino acids in length or a detectable fragment of full-length SARS-CoV-2 S1 protein that does not comprise the RBD. In some embodiments, the first surface is free of a fragment of full-length SARS-CoV-2 S1 protein greater than 300 amino acids in length or a fragment of full-length SARS-CoV-2 S1 protein that does not comprise the RBD. In certain embodiments of the test system, the first surface is substantially free from full length SARS-CoV-2 S1 antigen. In certain embodiments of the test system, the first surface comprises less than about 5%, less than about 4%, less than about 3%, less than about 2%, or less then about 1% of immobilized full length SARS-CoV-2 S1 antigen, relative to immobilized SARS-CoV-2 RBD antigen immobilized. In some embodiments, the first surface is free of detectable full length SARS-CoV-2 S1 antigen. In some embodiments, the first surface is free of full length SARS-CoV-2 S1 antigen. In certain embodiments of the test system, the first surface is substantially free from the SARS-CoV-2 S2 antigen. In certain embodiments of the test system, the first surface comprises less than about 5%, less than about 4%, less than about 3%, less than about 2%, or less then about 1% of immobilized SARS-CoV-2 S2 antigen, relative to immobilized SARS-CoV-2 RBD antigen. In some embodiments, the first surface is free of detectable SARS-CoV-2 S2 antigen. In some embodiments, the first surface is free of SARS-CoV-2 S2 antigen.

In certain embodiments of the test system, the second surface is substantially free from full-length SARS-CoV-2 spike protein. In certain embodiments of the test system, the second surface comprises less than about 5%, less than about 4%, less than about 3%, less than about 2%, or less then about 1% of immobilized full-length SARS-CoV-2 spike protein relative to immobilized SARS-CoV-2 RBD antigen. In some embodiments, the second surface is free of detectable full-length SARS-CoV-2 spike protein. In some embodiments, the second surface is free of full-length SARS-CoV-2 spike protein. In certain embodiments of the test system, the second surface is substantially free from full-length SARS-CoV-2 S1 protein. In certain embodiments of the test system, the second surface comprises less than about 5%, less than about 4%, less than about 3%, less than about 2%, or less then about 1% of immobilized full-length SARS-CoV-2 S1 protein relative to immobilized SARS-CoV-2 S2 antigen. In some embodiments, the second surface is free of detectable full-length SARS-CoV-2 S1 protein. In some embodiments, the second surface is free of full-length SARS-CoV-2 S1 protein. In certain embodiments of the test system, the second surface is substantially free from a fragment of full-length SARS-CoV-2 S1 protein greater than 300 amino acids in length or a fragment of full-length SARS-CoV-2 S1 protein that does not comprise the RBD. In certain embodiments of the test system, the second surface comprises less than about 5%, less than about 4%, less than about 3%, less than about 2%, or less then about 1% of a fragment of immobilized full-length SARS-CoV-2 S1 protein greater than 300 amino acids in length or an immobilized fragment of full-length SARS-CoV-2 S1 protein that does not comprise the RBD, relative to immobilized SARS-CoV-2 RBD antigen immobilized. In some embodiments, the second surface is free of a detectable fragment of full-length SARS-CoV-2 S1 protein greater than 300 amino acids in length or a detectable fragment of full-length SARS-CoV-2 S1 protein that does not comprise the RBD. In some embodiments, the second surface is free of a fragment of full-length SARS-CoV-2 S1 protein greater than 300 amino acids in length or a fragment of full-length SARS-CoV-2 S1 protein that does not comprise the RBD.

In certain embodiments of the test system, the first surface is contained within a first well and the second surface is contained in a second well. In some embodiments, the first and second surfaces are spatially distinct from each other. In some embodiments, the first and second wells are spatially distinct from each other.

In another aspect of the disclosure, the test system comprising: a first well comprising: an immobilized first binding moiety that specifically binds to a constant region of human IgG, an immobilized second binding moiety that specifically binds to a constant region of human IgA and an immobilized third binding moiety that specifically binds to a constant region of human IgM; a first biological sample from a host; and a first antigen comprising an amino acid sequence of at least 50 amino acids in length and less than 300 amino acids in length that has at least 99% identity to the amino acid sequence of the severe acute respiratory syndrome coronavirus 2 (SARS-CoV-2) receptor binding domain (RBD) antigen, wherein the first antigen comprises a detectable moiety; and a second well comprising: an immobilized first binding moiety that specifically binds to a constant region of human IgG, an immobilized second binding moiety that specifically binds to a constant region of human IgA and an immobilized third binding moiety that specifically binds to a constant region of human IgM; a second biological sample from the host; and a second antigen an amino acid sequence of at least 100 amino acids in length and less than 600 amino acids in length that has at least 99% identity to the amino acid sequence of the SARS-CoV-2 S2 antigen, wherein the second antigen comprises a detectable moiety.

As used herein, the term "biological sample" refers to a specimen taken from a human subject. Specimens may include, but are not limited to, serum, blood, plasma, sputum, urine, semen, mucous, sweat and tears.

As used herein, the term "host" refers to a human subject. The human subject can be suspected of having been infected with SARS-CoV-2. In some embodiments, the host is greater than 18 years of age.

In some embodiments, a test system comprises immobilized binding moieties that specifically binds human IgG, IgA and/or IgM, a first antigen comprising an amino acid sequence of at least 50 amino acids in length and less than 300 amino acids in length that has at least 99% identity to the amino acid sequence of the SARS-CoV-2 RBD antigen and a second antigen comprising an amino acid sequence of at least 100 amino acids in length and less than 600 amino acids in length that has at least 99% identity to the amino acid sequence of the SARS-CoV-2 S2 antigen. In some embodiments, the first and second antigens further comprises detectable labels. In certain embodiments, these labels are distinct.

Kits

In another aspect, the disclosure provides a kit, comprising the test system recited above, comprising: the first antigen; the second antigen; and the first binding moiety, the second binding moiety, and the third binding moiety, in separate containers. In some embodiments, kits comprise SARS-CoV-2 RBD antigen immobilized onto a first surface and SARS-CoV-2 S2 antigen immobilized onto a second surface. In some embodiments, the kit also comprises one or more binding moieties that specifically bind to one of human IgG, IgA and/or IgM. In some embodiments, these kits may be used for identifying the association of neutralizing antibodies in a human biological sample with SARS-CoV-2 antigens. In some embodiments, the kit comprises a washing solution or instructions for making a washing solution, wherein the combination of the antigen immobilized on the surfaces and the binding moieties with the washing solution allows detection of the interaction of neutralizing antibodies in a human biological sample with SARS-CoV-2 antigens.

In certain embodiments, a kit may further comprise instructions for suitable operational parameters in the form of a label or a separate insert. For example, the kit may have standard instructions informing a consumer/kit user how to use the kit.

The kits provided herein may optionally comprise a standard or control information, and/or a control amount of material, so that the test sample can be compared with the control information standard and/or control amount to determine if the test amount of neutralizing antibodies to SARS-CoV-2 antigens detected in a sample is an amount consistent with a diagnosis of previous infection with SARS-CoV-2.

Methods for Detecting the Presence of Host Antigen-Specific Antibodies that Specifically Bind SARS-CoV-2

In one aspect, the disclosure provides a method for detecting the presence of host antigen-specific antibodies that specifically bind SARS-CoV-2, the method comprising the steps of: 1) exposing a first biological sample from the host to a first surface comprising a first antigen comprising an amino acid sequence of at least 50 amino acids in length and less than 300 amino acids in length that has at least 99% identity to the amino acid sequence of the severe acute respiratory syndrome coronavirus 2 (SARS-CoV-2) receptor binding domain (RBD) antigen; 2) incubating the first surface with a first binding moiety that specifically binds to a constant region of human IgG, a second binding moiety that specifically binds to a constant region of human IgA and a third binding moiety that specifically binds to a constant region of human IgM; 3) detecting binding of one or more of the first, second and third binding moieties at the first surface to host antigen-specific antibodies, which generates a first signal; 4) exposing a second biological sample from the host to a second surface comprising a second antigen an amino acid sequence of at least 100 amino acids in length and less than 600 amino acids in length that has at least 99% identity to the amino acid sequence of the SARS-CoV-2 S2 antigen; 5) incubating the first surface with a fourth binding moiety that specifically binds to a constant region of human IgG, a fifth binding moiety that specifically binds to a constant region of human IgA and a sixth binding moiety that specifically binds to a constant region of human IgM; and 6) detecting binding of one or more of the fourth, fifth and sixth binding moieties at the second surface to host antigen-specific antibodies, which generates a second signal, thereby detecting the presence of host antigen-specific antibodies that specifically bind SARS-CoV-2.

In some embodiments, the SARS-CoV-2 RBD antigen comprises or consists of an amino acid sequence of at least 50 amino acids in length and less than 300 amino acids in length that has at least 99% identity to the amino acid sequence of SEQ ID NO:1. In some embodiments, the first antigen comprises the amino acid sequence of SARS-CoV-2 RBD antigen. In certain embodiments of the test system, the first antigen consists of the amino acid sequence of SARS-CoV-2 RBD antigen In some embodiments, the SARS-CoV-2 S2 antigen comprises or consists of an amino acid sequence of at least 100 amino acids in length and less than 600 amino acids in length that has at least 99% identity to SEQ ID NO:3. In certain embodiments of the test system, the second antigen comprises the amino acid sequence of SARS-CoV-2 S2 antigen. In certain embodiments of the test system, the second antigen consists of the amino acid sequence of SARS-CoV-2 S2 antigen.

In certain embodiments of the method, the binding moieties are antibodies or fragments thereof.

In certain embodiments of the method, the first, second, third, fourth, fifth and sixth binding moieties further comprise a detectable moiety.

In certain embodiments of the method, the detectable moiety is a chromogenic label. In certain embodiments of the test system, the detectable moiety is a fluorescent label.

In certain embodiments of the method, the chromogenic label comprises horseradish peroxidase (HRP). In certain embodiments of the method, incubation of the first, second or third binding moieties with an HRP substrate produces a colormetric signal.

In some embodiments, the HRP substrate is selected from the group consisting of 3,3',5,5'-Tetramethylbenzidine (TMB), o-Phenylenediamine dihydrochloride (OPD), and 2,2'-Azinobis [3-ethylbenzothiazoline-6-sulfonic acid]-diammonium salt (ABTS).

In some embodiments, the chromogenic label comprises Alkaline Phosphatase (Alk-phos). In some embodiments, the Alk-phos substrate comprises para-nitrophenylphosphate (pNPP).

In some embodiments, the chromogenic label comprises β-Galactosidase (β-gal). In some embodiments, the β-gal substrate comprises a β-galactoside, such as ortho-nitrophenyl-β-galactoside (ONPG) or 5-bromo-4-chloro-3-indolyl-β-d-galactopyranoside (X-gal).

In some embodiments, the chromogenic label comprises a urease. In some embodiments, the urease substrate comprises Urea bromocresol.

In certain embodiments of the method, the first binding moiety is the same as the fourth binding moiety, the second binding moiety is the same as the fifth binding moiety and/or the third binding moiety is the same as the sixth binding moiety.

In certain embodiments of the method, the first surface is substantially free from full-length SARS-CoV-2 spike protein.

In certain embodiments, the first surface is substantially free from full-length SARS-CoV-2 spike protein. As used herein, the term "substantially free" refers to an amount of a molecule that does not affect the rate of positive, intermediate and negative results produced by the test system or methods of using the test system described herein. In some embodiments, the term "substantially free" refers to the presence of a contaminant at less than about 5%, less than about 4%, less than about 3%, less than about 2%, or less then about 1% of a total composition. In certain embodiments of the test system, the first surface comprises less than about 5%, less than about 4%, less than about 3%, less than about 2%, or less then about 1% of immobilized full-length SARS-CoV-2 spike protein relative to immobilized SARS-CoV-2 RBD antigen. In some embodiments, the first surface is free of detectable full-length SARS-CoV-2 spike protein. In some embodiments, the first surface is free of full-length SARS-CoV-2 spike protein.

In certain embodiments, the first surface is substantially free from a fragment of full-length SARS-CoV-2 S1 protein greater than 300 amino acids in length or a fragment of full-length SARS-CoV-2 S1 protein that does not comprise the RBD. In certain embodiments, the first surface comprises less than about 5%, less than about 4%, less than about 3%, less than about 2%, or less then about 1% of an immobilized fragment of full-length SARS-CoV-2 S1 protein greater than 300 amino acids in length or a fragment of full-length SARS-CoV-2 S1 protein that does not comprise the RBD, relative to immobilized SARS-CoV-2 RBD antigen. In some embodiments, the first surface is free of a detectable fragment of full-length SARS-CoV-2 S1 protein greater than 300 amino acids in length or a detectable fragment of full-length SARS-CoV-2 S1 protein that does not comprise the RBD. In some embodiments, the first surface is free of a fragment of full-length SARS-CoV-2 S1 protein greater than 300 amino acids in length or a fragment of full-length SARS-CoV-2 S1 protein that does not comprise the RBD. In certain embodiments, the first surface is substantially free from full length SARS-CoV-2 S1 antigen. In certain embodiments, the first surface comprises less than about 5%, less than about 4%, less than about 3%, less than about 2%, or less then about 1% of immobilized full length SARS-CoV-2 S1 antigen, relative to immobilized SARS-CoV-2 RBD antigen immobilized. In some embodiments, the first surface is free of detectable full length SARS-CoV-2 S1 antigen. In some embodiments, the first surface is free of full length SARS-CoV-2 S1 antigen. In certain embodiments, the first surface is substantially free from the SARS-CoV-2 S2 antigen. In certain embodiments, the first surface comprises less than about 5%, less than about 4%, less than about 3%, less than about 2%, or less then about 1% of immobilized SARS-CoV-2 S2 antigen, relative to immobilized SARS-CoV-2 RBD antigen. In some embodiments, the first surface is free of detectable SARS-CoV-2 S2 antigen. In some embodiments, the first surface is free of SARS-CoV-2 S2 antigen.

In certain embodiments, the second surface is substantially free from full-length SARS-CoV-2 spike protein. In certain embodiments, the second surface comprises less than about 5%, less than about 4%, less than about 3%, less than about 2%, or less then about 1% of immobilized full-length SARS-CoV-2 spike protein relative to immobilized SARS-CoV-2 RBD antigen. In some embodiments, the second surface is free of detectable full-length SARS-CoV-2 spike protein. In some embodiments, the second surface is free of full-length SARS-CoV-2 spike protein. In certain embodiments, the second surface is substantially free from full-length SARS-CoV-2 S1 protein. In certain embodiments, the second surface comprises less than about 5%, less than about 4%, less than about 3%, less than about 2%, or less then about 1% of immobilized full-length SARS-CoV-2 S1 protein relative to immobilized SARS-CoV-2 S2 antigen. In some embodiments, the second surface is free of detectable full-length SARS-CoV-2 S1 protein. In some embodiments, the second surface is free of full-length SARS-CoV-2 S1 protein. In certain embodiments, the second surface is substantially free from a fragment of full-length SARS-CoV-2 S protein greater than 300 amino acids in length or a fragment of full-length SARS-CoV-2 S1 protein that does not comprise the RBD. In certain embodiments, the second surface comprises less than about 5%, less than about 4%, less than about 3%, less than about 2%, or less then about 1% of a fragment of immobilized full-length SARS-CoV-2 S1 protein greater than 300 amino acids in length or an immobilized fragment of full-length SARS-CoV-2 S1 protein that does not comprise the RBD, relative to immobilized SARS-CoV-2 RBD antigen immobilized. In some embodiments, the second surface is free of a detectable fragment of full-length SARS-CoV-2 S1 protein greater than 300 amino acids in length or a detectable fragment of full-length SARS-CoV-2 S1 protein that does not comprise the RBD. In some embodiments, the second surface is free of a fragment of full-length SARS-CoV-2 S1 protein greater than 300 amino acids in length or a fragment of full-length SARS-CoV-2 S1 protein that does not comprise the RBD.

In certain embodiments of the method, the first surface is contained within a first well and the second surface is contained in a second well. In some embodiments, the first and second surfaces are spatially distinct from each other. In some embodiments, the first and second wells are spatially distinct from each other.

In certain embodiments of the method, the biological sample is selected from the group consisting of serum, blood, plasma, sputum, urine, semen, mucous, sweat and tears.

In certain embodiments, the method comprises an enzyme-linked immunosorbent assay (ELISA).

In some embodiments, the method uses a test system comprises immobilized binding moieties that specifically binds human IgG, IgA and/or IgM, a first antigen comprising an amino acid sequence of at least 50 amino acids in length and less than 300 amino acids in length that has at least 99% identity to the amino acid sequence of the SARS-CoV-2 RBD antigen and a second antigen comprising an amino acid sequence of at least 100 amino acids in length and less than 600 amino acids in length that has at least 99% identity to the amino acid sequence of the SARS-CoV-2 S2 antigen. In some embodiments, the first and second antigens further comprises detectable labels. In certain embodiments, these labels are distinct. The test system can be used in one or more wells. In some embodiments of a one well system, each of the first and second antigens would require distinct labels. In some embodiments, a biological sample from a host would be exposed to the immobilized binding moieties, thereby binding IgG, IgA and/or IgM from the biological sample. In some embodiments, the non-binding portion of the sample could then be washed away. In some embodiments, the labeled first antigen would be exposed to the immobilized binding moiety. If any of the immobilized antibodies from the biological sample specifically bound the first antigen, the label associated with the first antigen could be detected. In some embodiments, this detection would occur after a first washing step. In some embodiments, the immobilized binding moieties would be exposed to the labeled second antigen. In some embodiments, this could occur in the same well that the first antigen was added to or to a distinct well with a distinct surface. If any of the immobilized antibodies from the biological sample specifically bound the second antigen, the label associated with the second antigen could be detected. In some embodiments, this detection would occur after a first washing step. The label associated with the first antigen would generate a first signal and the label associated with the second antigen would generate a second signal.

In certain embodiments, the method is capable of detecting the presence of host antigen-specific IgG antibodies that specifically bind SARS-CoV-2. In certain embodiments, the method is capable of detecting the presence of host antigen-specific IgA antibodies that specifically bind SARS-CoV-2. In certain embodiments, the method is capable of detecting the presence of host antigen-specific IgM antibodies that specifically bind SARS-CoV-2. In certain embodiments, the method is capable of simultaneously detecting the presence of host antigen-specific IgG, IgA, and IgM antibodies that specifically bind SARS-CoV-2.

In some embodiments, the first signal is associated with finding IgG, IgA and/or IgM antibodies in a biological sample from a host that specifically bind to the SARS-CoV-2 RBD antigen. In some embodiments, the second signal is associated with finding IgG, IgA and/or IgM antibodies in a biological sample from a host that specifically bind to the SARS-CoV-2 S2 antigen.

In certain embodiments of the method, a first signal value that is at least five standard deviations above a negative control sample indicates a first positive result; a first signal value that is at least three standard deviations but less than five standard deviations above a negative control sample indicates a first indeterminate result; a first signal value that is less than three standard deviations above a negative control sample indicates a first negative result; a second signal value that is at least five standard deviations above a negative control sample indicates a second positive result; a second signal value that is at least three standard deviations but less than five standard deviations above a negative control sample indicates a second indeterminate result; and a second signal value that is less than three standard deviations above a negative control sample indicates a second negative result.

In some embodiments, a negative control sample is a biological sample from a host that has not been infected with SARS-CoV-2. In some embodiments, the biological sample used as a negative control sample was taken from a host before SARS-CoV-2 infected humans. In some embodiments, the biological sample used as a negative control sample was taken from a human who has tested negative for SARS-CoV-2. In some embodiments, the test used was a PCR based test from a nasal sample from the host. In some embodiments, the test used was an antibody based test.

In certain embodiments of the method, a first positive result and a second positive result indicates the presence of host antigen-specific antibodies. In certain embodiments of the method, a first positive result and a second indeterminate result indicates the presence of host antigen-specific antibodies. In certain embodiments of the method, a first positive result and a second negative result indicates an absence of host antigen-specific antibodies. In certain embodiments of the method, a first indeterminate result and a second negative result indicates an absence of host antigen-specific antibodies.

In certain embodiments of the method, the host antigen-specific antibodies are neutralizing host antigen-specific antibodies that specifically bind SARS-CoV-2.

In certain embodiments of the method, if there is no first positive result, steps 4-6 are not performed.

EXAMPLES

Example 1—Serological Assay for Spike Protein Receptor Binding Domain (RBD) Antibodies Severe acute respiratory syndrome coronavirus 2 (SARS-CoV-2) causes infection of the respiratory tract, triggering an immune response and antibody production directed towards viral antigens within 1-2 weeks of exposure and symptom onset. Such antibodies can be detected in the serum and plasma of subjects with ongoing infections and those with prior exposures. Accurately measuring the presence of SARS-CoV-2 specific antibodies, including neutralizing SARS-CoV-2 specific antibodies, is important for determining if a subject has been exposed to SARS-CoV-2 and acquired immunity.

The following parameters and reagents were used in the development of an anti-SARS-CoV-2 RBD antibody detection assay.

Sample Characteristics Used in this Study
  Sample Type: Serum.
  Volume: >1 mL.
  Container: Whole blood collected in serum separator (SST) tube.
  Acceptable specimen: Serum should be separated from specimen within 90 minutes after collection. Tube should be at room temperature before centrifugation.
  Specimen Storage: Serum separated from whole blood, either by gel/SST or manual transfer, is stable for up to 3 days at room temperature; up to 1 week when refrigerated at 2-8° C.; and up to 6 months when frozen (−20° C. or lower).

Criteria for Rejecting Samples
  Specimens which are severely lipemic and hemolyzed.
  Improper handling or transport of specimens.
  Insufficient specimen volume or amount.
  Specimens that are mislabeled or lack unique identifiers.
  Lack of unique identifiers on the test order form.

Equipment Used in this Study
  Tabletop centrifuge capable of 3000×g.
  Beckman FX liquid hander workstation.
  BMG CLARIOstar Plus Plate Reader.
  BioTek Synergy 2.

Reagents and Consumables Used in this Study.
  Greiner bio-one High Binding 384 well microplate.
  Tubes without anti-coagulant (BD Vacutainer Serum Blood Collection Tubes Plastic 367988).
  Peroxidase AffiniPure Goat Anti-Human IgA+IgG+IgM (Jackson Immunoresearch code #109-035-064).
  3,3',5,5'-Tetramethylbenzidine (high sensitivity TMB; Fisher Scientific; AAJ61325AU).
  Recombinant spike protein receptor binding domain (RBD)
  Anti-COVID-19 & SARS-CoV S Glycoprotein [CR3022] (Absolute antibody Ab01680-10.0).
  ELISA Coating Buffer (1 L MiliQ $H_2O$, 8.4 g $NaHCO_3$, 10.6 g $Na_2CO_3$).
  PBS-T Wash Buffer.
  2N Sulfuric Acid.
  PBS (Fisher Scientific; SH30256LS).
  Non-fat dry milk (Thermo Fisher; NC9121673).

Methodology
The test for antibodies specific for the severe acute respiratory syndrome coronavirus 2 (SARS-CoV2) involved quantifying serum reactivity against viral proteins (e.g., SARS-CoV-2 RBD antigen). Serum was obtained from blood samples, diluted, and added to plates coated with recombinant RBD. Antibodies in the serum were allowed to bind to the RBD and were then detected by a secondary detection antibody and a colorimetric substrate. The intensity of color was quantified by absorbance values at 450 nm wavelength. Qualitative presence or absence calls in the validation study were made and reported based on negative control naïve sera obtained from human subjects prior to August 2019 and positive control sera from microbiologically confirmed subjects.

Serological testing of antibodies described herein used an enzyme-linked immunosorbent assay (ELISA). The first step in the ELISA was to coat RBD antigens on high protein-binding 384 well plates in mildly alkaline solutions. This step immobilized the target antigen onto the plate and allowed for subsequent solution exchange and washing without measurable loss of the protein antigen. After removal of the coating solution, wells were then treated with powdered milk solutions to block all other protein-binding sites on the plate. After the blocking step, solutions in the wells were removed and diluted serum was added. Serum contains high concentrations of antibodies. If the subject has been exposed to SARS-CoV-2, a portion of these serum antibodies will be specific for the spike protein and bind to the protein coated on the plate. After washing, secondary antibodies specific for the constant region of human immunoglobulins were added. These secondary antibodies were covalently conjugated to the enzyme horseradish peroxidase (HRP). After washing again, a colorimetric substrate called 3,3',5,5'-tetramethylbenzidine (TMB) was added for 3 minutes. Horseradish peroxidase converts this substrate to a blue color. Thus, if the coating antigen (e.g., RBD) is bound by serum antibodies, which are in turn bound by the enzyme-linked secondary antibody, the solution in the well will turn to a blue color. The reaction was then quenched and the absorbance at 450 nm was measured through spectrophotometry. The signal at 450 nm is thus proportional to the concentration of spike protein RBD-specific serum antibodies.

Control Samples Used in this Study
Each assay used the following control samples:
  Human serum from patients confirmed COVID19+ with molecular testing.
  Human serum collected prior to 2019.
  Anti-COVID-19 & SARS-CoV S Glycoprotein (Positive Control).
  Negative Template Control (HPLC $H_2O$).

TABLE 1

Expected Performance of Controls Included in the SARS-CoV-2 antibody diagnostic ELISA assay

| Control Type | External Control Name | Used to Monitor | Expected $OD_{450nm}$ Values |
|---|---|---|---|
| Negative | Naïve Serum | Proper blocking and washing; baseline of 'noise' in the assay. | <0.3 |
| Positive | SARS-CoV-2 S | Substantial reagent failure | >0.7 |

TABLE 1-continued

Expected Performance of Controls Included in the SARS-CoV-2 antibody diagnostic ELISA assay

| Control Type | External Control Name | Used to Monitor | Expected $OD_{450nm}$ Values |
|---|---|---|---|
| | Glycoprotein | including positive control serum, spike protein, secondary antibody, and TMB integrity | |

Validation Samples Used in this Study

The following samples were tested in the above described assay for validation.

Washington University—St. Louis Samples

21 PCR-confirmed serum specimens were received from Washington University—St. Louis.

SUBJECT INCLUSION CRITERIA—Washington University samples 1) 18 years of age or older;
2) Prior diagnosis of COVID-19 documented through molecular testing by a laboratory test
3) Complete resolution of symptoms at least 14 days prior to donation; and
4) Able to provide informed consent.

SUBJECT EXCLUSION CRITERIA—Washington University samples

1) Participants who are <18 years of age;
2) Known diagnosis of HIV, active HBV (positive HBV sAg) or active HCV (positive HCV RNA);
3) Participants who are prisoners;
4) Have received immunoglobulin or other blood products, with the exception of Rho D immunoglobulin, within 90 days prior to study enrollment;
5) Have donated blood or blood products within 30 days before study enrollment; and
6) Any condition in the opinion of the investigator that would interfere with the proper conduct of the trial.

University of Arizona Campus Health Samples 9 samples collected from patients confirmed positive for SARS-CoV-2 using molecular testing. Serum samples collected >16 days since symptom onset.

2 serum specimens were received from patients who presented symptoms Mar. 21, 2020 and Mar. 23, 2020, respectively but tested negative with molecular testing from a nasal swab. Serum from these patients used in this study was collected Apr. 16, 2020.

University of Arizona Health Sciences (UAHS) Biorepository Samples

32 Serum specimens were received from the UAHS Biorepository that had been collected between March-July 2019, prior to the onset of SARS-CoV-2 in the human population.

These specimens were treated as true negatives.

Serum Sample Plate Used in Validation Study

The serum plate for testing included 21 presumed positive specimens received from Washington University, 9 presumed positive and 2 presumed negative specimens received from UA Campus Health, and 32 true negative samples received from the UAHS Biorepository. The plate also contained 29 non-treatment control (NTC) water samples and 3 Human ACE2 Fc Positive Controls.

The 29 NTC samples on the plate were used to determine the assay's Limit of Detection (LoD); expressed as the analyte concentration corresponding to the sample blank value plus three standard deviation.

Validation Study Strategy

The Validation Study Serum sample configuration containing 30 presumed positive samples, 2 presumed negative samples, 32 true negative samples, 3 positive controls and 29 buffer (NTC) controls were plated into a microtiter plate coated with the RBD Spike protein the previous day. All ELISA preparation steps (blocking, diluting, transfer to 384-well ELISA plate, addition of secondary antibody and development) were performed by an automated method on a Beckman FX liquid-handling robot. In the method, each sample was replicated four times in a 384-well ELISA plate; two duplicates at a 1:20 dilution and 2 duplicates at a 1:40 dilution. The ELISA plate was then read on both a CLAIROStar Plate Reader and a BioTek Synergy 2 at an absorbance of 450 nm (within 1 hour after adding 2N Sulfuric Acid). To test the reproducibility of the assay each 384-well plate was run four times; twice by one technician, and twice by another, each working on two different days.

Results

Initial review of these data suggest that the variation was slightly greater in the samples diluted 1:20 compared to those diluted 1:40. All following analyses use the 1:40 dilution results and this dilution will be used in the testing service Standard Operating Procedures.

One of the two presumed negative specimens fell within the range of the weakest signal presumed positive specimens. This patient presented clinical symptoms of SARS-CoV-2 but was negative for the virus using a molecular test. Serum was collected for this study 26 days after patient exhibited symptoms. For establishment of thresholds for detecting positive and negative samples in the following analyses, only the 30 true negative specimens were used and the two presumed negatives were excluded. These two specimens were then considered in test accuracy results after testing thresholds for interpretation were determined.

Figure 2:
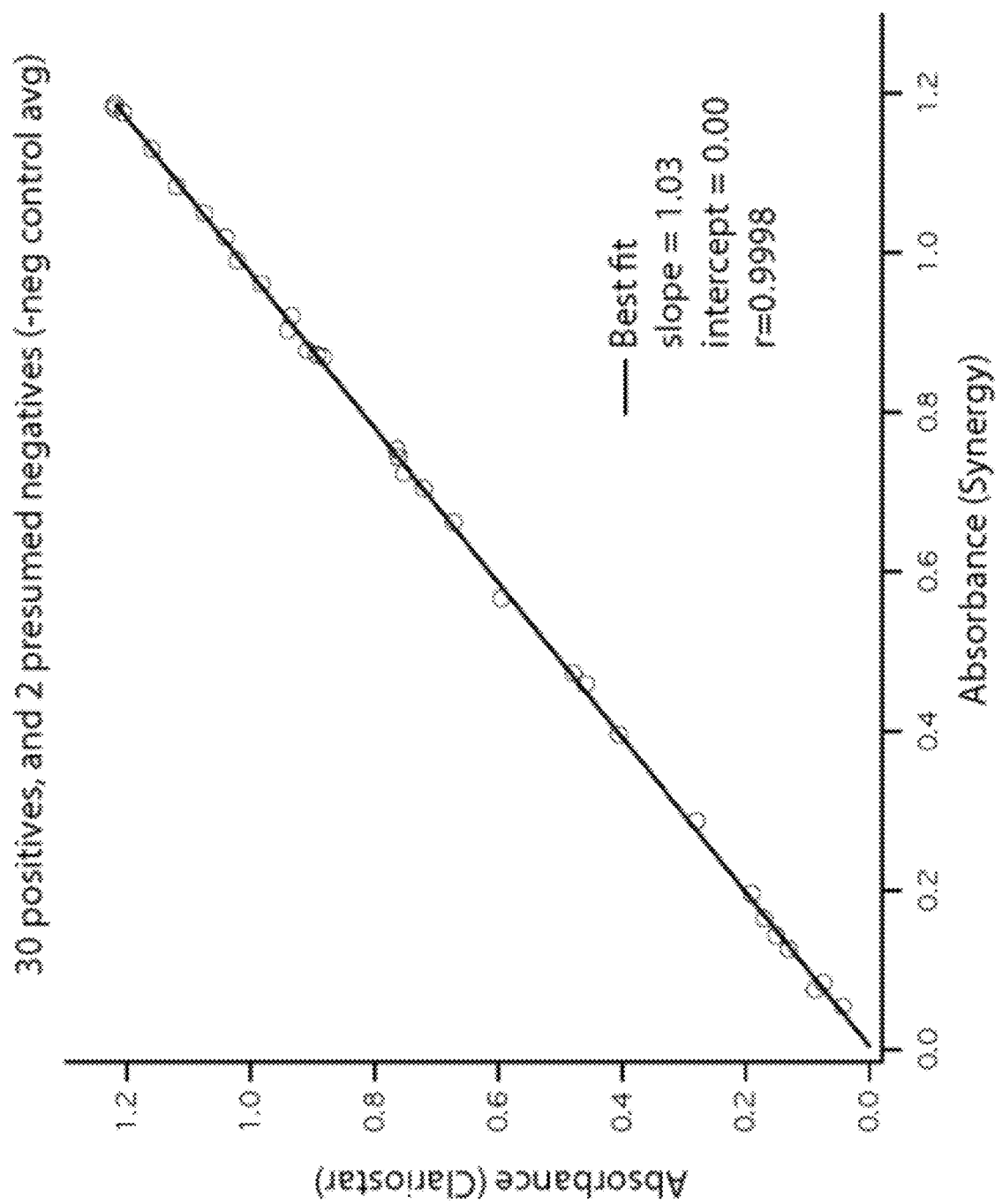

To determine reliability between different plate readers, the Synergy Plate Reader and CLAIROStar Plate Reader were compared. Results from both instruments were tightly correlated (FIG. 2; $r^2=0.9996$) and these instruments may be used interchangeably, following the established protocol of using the average OD reading negative serum controls on each plate to determine the threshold for reporting positive results for that plate. Results presented for only the CLAIROStar instrument in the remainder of this study.

Figure 3:
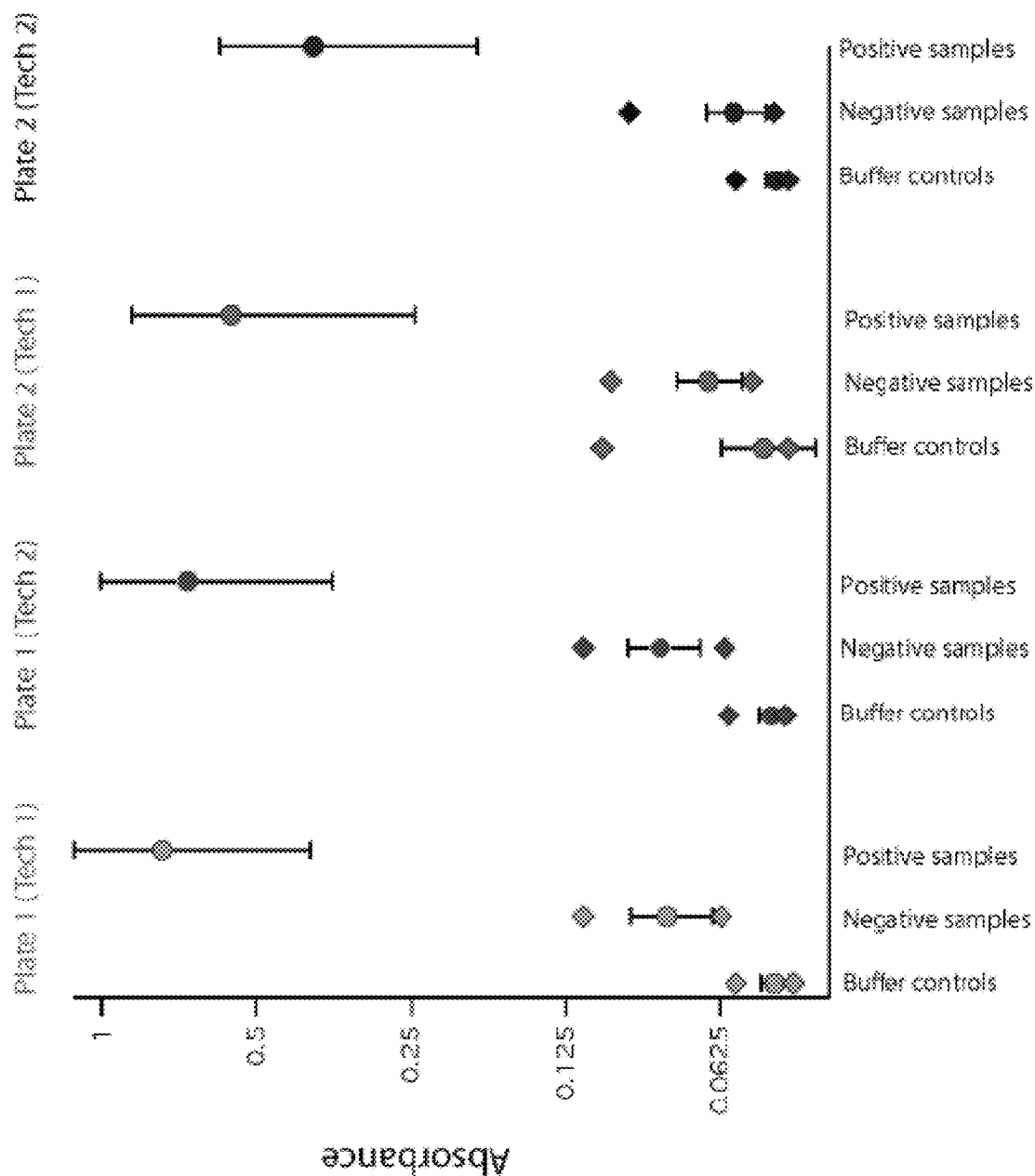

To determine day-to-day and technician-to-technician variation, samples were tested on different days and by different technicians. As shown in FIG. 3, there was minimal variation observed between days and technicians during this study, and only in the average absorbance of sample groups and did not affect result interpretation. Differences in absorbance across these variables was scalar, such that lower positive read values were associated with lower negative read values.

To determine the precision of the assay, the average and standard deviation of absorbance reading were compared. The signal from the NTC (buffer) controls were all close to $4.9 \pm 0.3 \times 10^{-2}$ (Table 2). Samples taken from patients before the COVID-19 outbreak (negative samples) were, on average, 5-10 standard deviations (error from the buffer controls) above the buffer controls, while samples taken from patients that have tested positive for SARS-CoV-2 in a molecular test, were on average, 150-240 standard deviations above the control.

TABLE 2

The average and standard deviation of absorbance readings for each group of samples.

|  | Plate 1 (Tech 1) | Plate 1 (Tech 2) | Plate 2 (Tech 1) | Plate 2 (Tech 2) |
|---|---|---|---|---|
| Buffer controls | 4.9 ± 0.3 × $10^{-2}$ | 5.0 ± 0.3 × $10^{-2}$ | 4.9 ± 0.3 × $10^{-2}$ | 4.9 ± 0.2 × $10^{-2}$ |
| Negative samples | 7.9 ± 1.3 × $10^{-2}$ | 8.1 ± 1.3 × $10^{-2}$ | 6.6 ± 1.0 × $10^{-2}$ | 5.9 ± 0.8 × $10^{-2}$ |
| Positive samples | 77 ± 37 × $10^{-2}$ | 68 ± 32 × $10^{-2}$ | 56 ± 32 × $10^{-2}$ | 39 ± 20 × $10^{-2}$ |

To determine the accuracy of the ELISA assay the data was analyzed for each individual sample across the four plates, calculating the average, standard deviation, and data range for all of the negative and positive controls. Here each value was normalized by subtracting the average value from the negative control. The data show (FIG. 4) that the values for the negative control samples were consistently lower than those found for the positive controls (which are ordered according to their average value).

To protect against reporting false negatives, a 3-standard deviation cut off was used (bottom "3 SD" line, FIG. 4) using a standard deviation of 1.5×$10^{-2}$ (larger than that seen in any of the experiments); Patients are considered negative below this threshold and this results in 32 negative samples as negative 4/4 times (that is on both plates for both technicians; 128 samples total). Above the 3 SD threshold, 26/30 positive samples report as positive 4/4 times. Four samples from patients that have tested positive for SARS-CoV-2, but have consistently low ELISA scores, only passed the three-standard deviation cut-off on 1-3 plates (one patient ¼ positives, two patients 2/4 positives, one patient ¾ positives). To reduce the potential for reporting false positive results, a 5-standard deviation cut off was incorporated (top "5 SD" line, FIG. 4) using a standard deviation of 1.5×$10^{-2}$. This results in 25/30 positives all four iterations and the category between 3-5 standard deviations (bottom and top lines) from the negative control average will be reported as "indeterminate". In employing this very conservative approach, the theoretical chance of calling false positives (based on a normal distribution of error) is 0.3% at 3 SD, and less than 1 in a million false positives at 5 SD.

Figure 4:
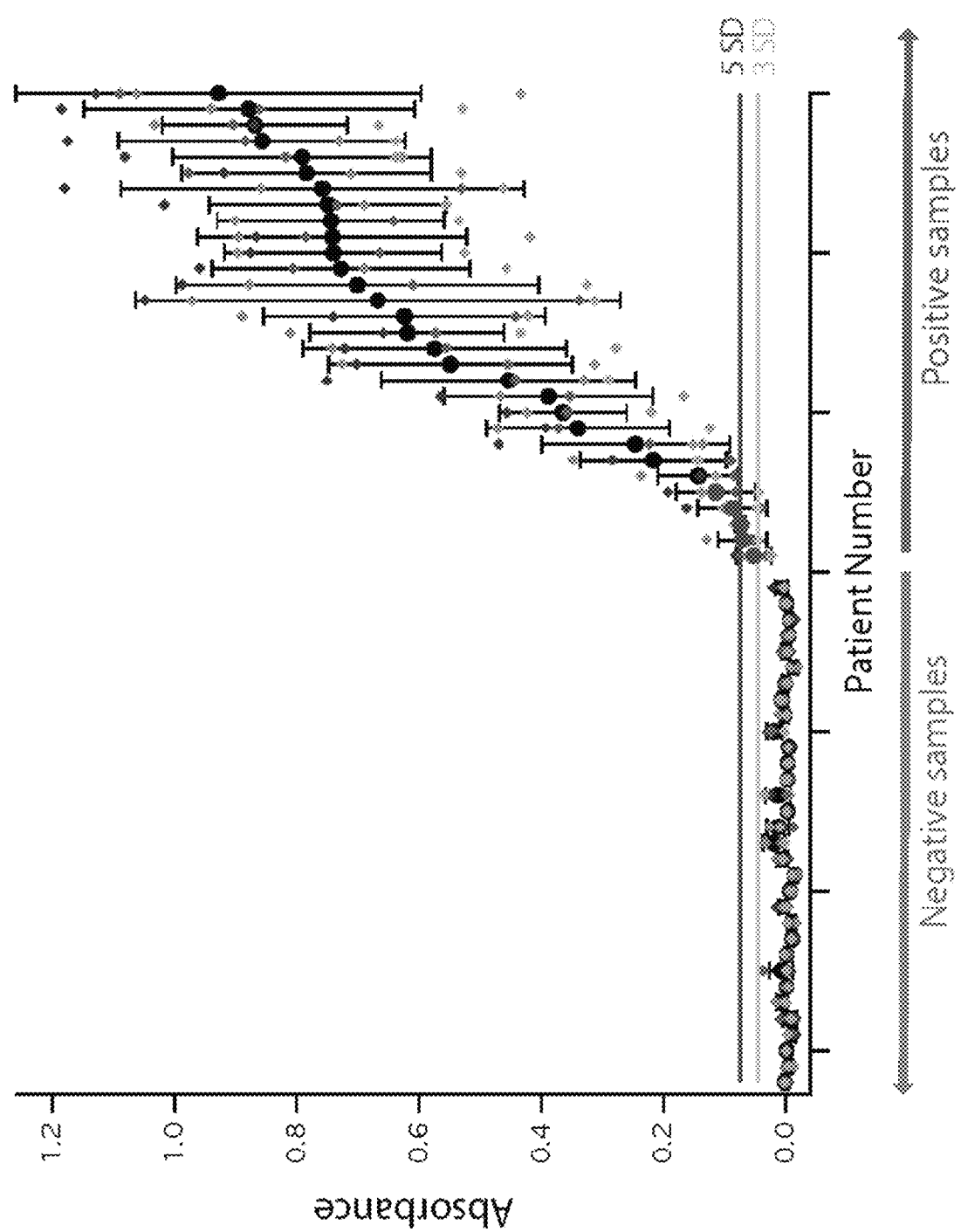

Five of the presumed positive samples with weak signal overlapped the positive/negative/indeterminate categories across multiple runs (FIG. 4, Table 3). For the two presumed negative specimens that were removed from analysis, under these thresholds one was reported negative 4/4 times and the other reported positive 2/4 and negative 2/4 times (never indeterminate).

TABLE 3

Results for presumed positive samples that fell outside of reporting thresholds over multiple iterations.

| Sample | Avg. OD | Negative | Indeterminate | Positive |
|---|---|---|---|---|
| WU-5 | 0.05 | 2 | 1 | 1 |
| WU-13 | 0.07 | 1 | 2 | 1 |
| UACH-11 | 0.07 | 0 | 2 | 2 |
| UACH-2 | 0.09 | 1 | 2 | 2 |
| WU-20 | 0.11 | 1 | 0 | 3 |

Sensitivity and specificity of the assay was also determined. Using the thresholds determined for calling positive and negative samples, the clinical agreement of our presumed positive and true negative samples was assessed. Sensitivity of the assay was determined to be 95.61% and Specificity was 100%. Positive and negative predictive values were 100% and 96.24%, respectively (Indeterminate samples removed). See Table 4 below for the results.

TABLE 4

Clinical agreement of the presumed positive and true negative samples with the assay ("UAGC-CS Abs Test") following determined cut of values for presenting positive and negative results.

|  |  | COVID-19 (PCR+) | | Sensitivity = 95.61% |
|---|---|---|---|---|
|  |  | Positive | Negative | Specificity = 100.00% |
| UAGC-CS Abs Test | Positive | 109 | 0 | Positive predictive value (PPV) = 100.00% |
|  | Negative | 5 | 128 | Negative predictive value (NPV) = 96.24% |

The limit of detection as assessed by the amount of 'background noise' inherent in the assay was calculated as an average absorbance OD reading of the NTC/Buffer control plus three standard deviation, and was determined to be 0.0058 OD at 450 nm.

Figure 5:
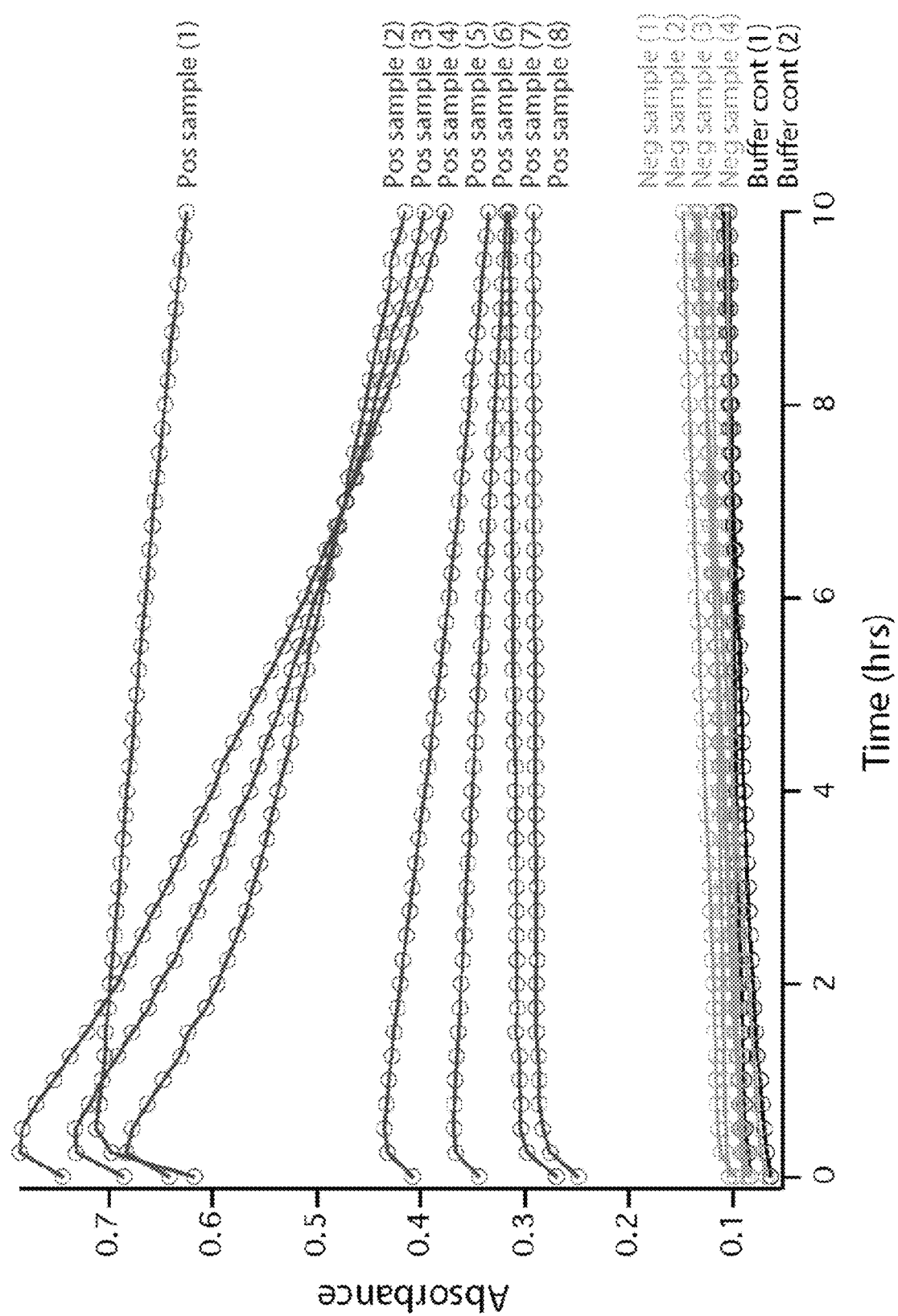

In this protocol, the absorbance is read on the plate reader within an hour of completing the final wash step. However, to assess if results may be skewed by time delays, a comparison of iterative run results (where the same plate was read every 15 minutes for 10 hours to assess changes in signal, was performed (FIG. 5; absorbance overtime). This was not performed on the Validation Serum Sample Plate used for the other analyses, but instead was done with a subset of samples run as a serial dilution (6 negative, 8 positive and 2 NTC) as was initially used to determine the dilution proportions used for the validation study plate runs. This experiment showed that while there is significant drift in the absorbance signal over time, the positive samples remained separated from the negative samples and buffer control samples during the entire time course.

Conclusions

These experiments show that the ELISA assay targeting antibodies receptive to the SARS-CoV-2 spike protein receptor binding domain (RBD) is both sensitive and accurate. The assay was determined compatible between both the CLAIROStar and BioTek Synergy 2 plate readers and uses a 1:40 dilution for serum samples. To reduce false positive results and increase accuracy of negative results, as determined thresholds for detection were used, including reporting of indeterminate results for samples that fall between these thresholds. The threshold for negative calls was below three standard deviations of the average of the negative serum controls included in each run and positive results were called above 5 standard deviations of that average. Indeterminate results fell between the two thresholds. Each assay plate was run with a minimum of 12 negative serum controls and the average for the run determined from these. A standard deviation of 0.015 as determined by assessing all iterations performed during this validation study was applied to each plate's average for the negative serum controls, as a conservative (and consistent) approach. Following these interpretation guidelines, the sensitivity of the assay was determined to be 95.61% and specificity was 100%. Positive and negative predictive values were 100% and 96.24%, respectively.

Example 2—Cross-Reactivity Evaluation and Updated Analytical Interpretation for the Serological Assay for Spike Protein Receptor Binding Domain (RBD) Antibodies An additional 320 negative specimens to the validation study of Example 1 were employed to assess cross-reactivity in the assay. In addition, neutralizations were performed on pilot study specimens to inform positive result reporting. The additional data sets new thresholds for result reporting for the SARS-CoV-2 ELISA pan-Ig Antibody Test. The threshold for reporting negative results were for samples with $OD_{450nm}$ of ≤0.120. The threshold for reporting positive results were for samples with $OD_{450nm}$ of ≥0.389. Indeterminate results fell between the two thresholds. Using these new thresholds, the clinical agreement of the assay was re-evaluated with the additional cross-reactivity samples included; sensitivity of the assay was determined to be 89.5% and specificity was 99.9%. Positive and negative predictive values were 98.7% and 99.1%, respectively.

The 320 new specimens were treated as true negatives; all specimens were collected between 2014-2019, prior to the onset of SARS-CoV-2 in the human population. These specimens were collected under an RB from the general population and presumed to have a high prevalence of vaccination against, and/or infection with expected cross-reactants (such as other coronaviruses).

Figure 6:
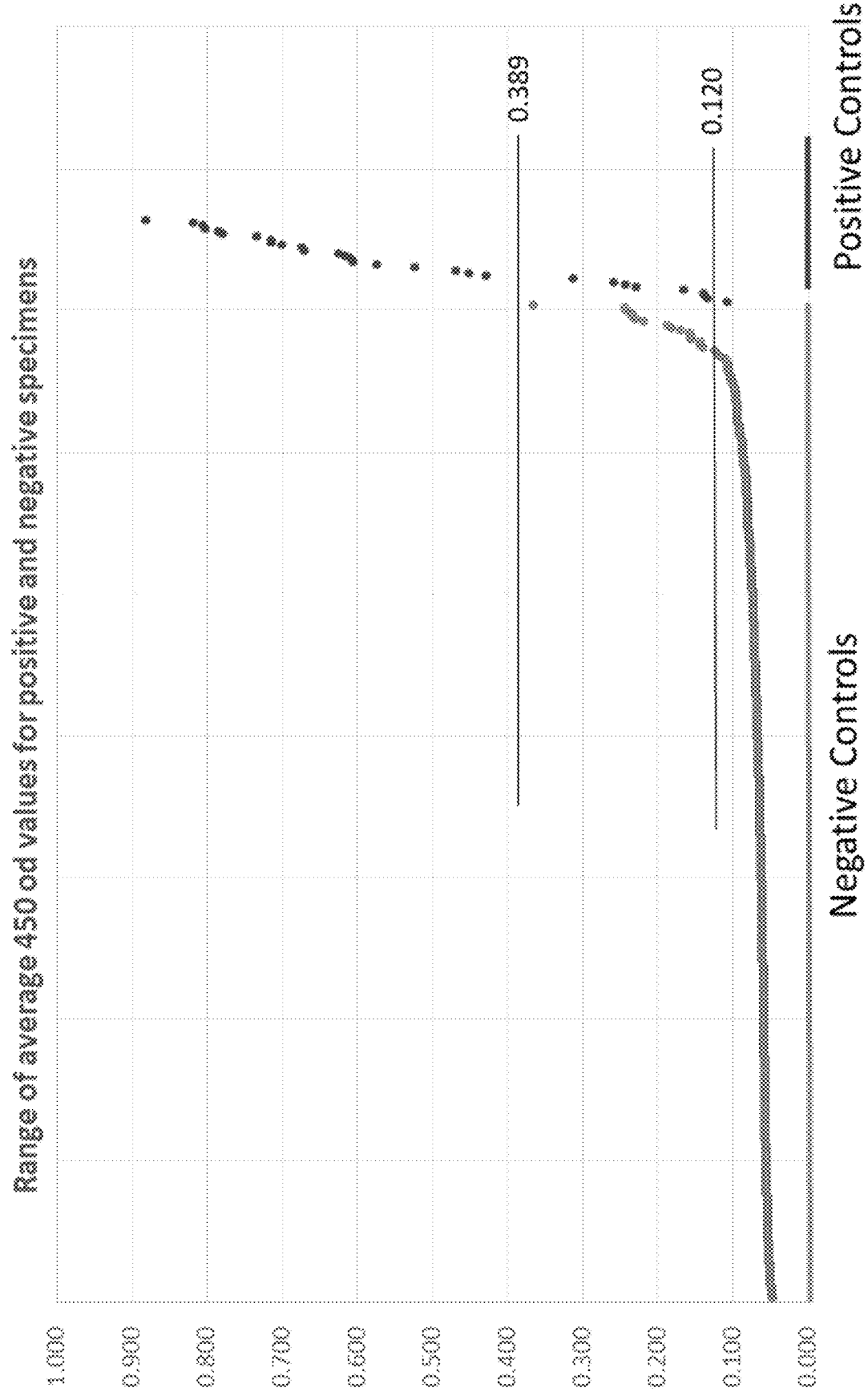

Three independent ELISAs following the established protocol were performed for each of the 320 specimens. The readings for this larger sample set extended the range of $OD_{450nm}$ values from what was previously observed in the initial validation of Example 1 with 30 negative specimens. Of the averages for 320 samples, 18 exceeded the previously established threshold of 0.12 $OD_{450nm}$ for negative specimens and 13 exceeded 0.15 $OD_{450nm}$, falling into the previously established "positive" category. One specimen average $OD_{450nm}$ was 0.37 (FIG. 6).

SARS-CoV-2 Neutralization Confirmation

Figure 7:
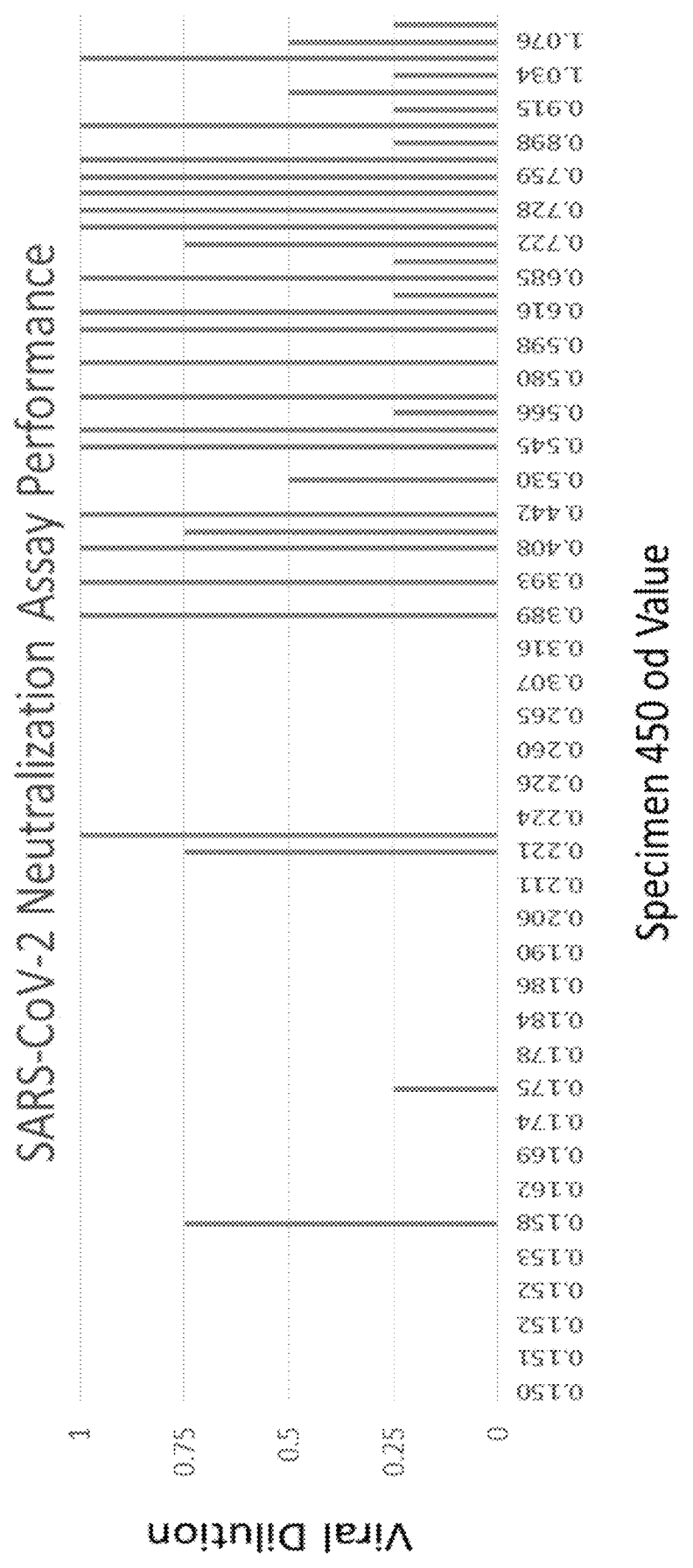

Through an initial pilot study using the validated "SARS-CoV-2 ELISA pan-Ig Antibody Test", performance through a neutralization assay was evaluated for 863 specimens. Neutralization assays using live virus were performed in dilution series of 100, 75, 50 and 25%. 30 out of 36 specimens at or above 0.389 $OD_{450nm}$ (83%) successfully neutralized, while only 6 of the remaining 827 specimens (0.73%) below 0.389 $OD_{450nm}$ neutralized (spanning $OD_{450nm}$ values of 0.083-0.175; FIG. 7). Although the neutralization assays were not clinically validated, these data help establish a correlation of the ELISA test to the patient's capacity of resistance and was used to establish a new positive call threshold for the assay at 0.389 $OD_{450nm}$.

Based on the cross-reactivity results and the performance of specimens using neutralization confirmation, the sensitivity and specificity was re-evaluated incorporating the additional 320 negative control samples and setting new thresholds for positive specimens to be ≥0.389 and negatives to be ≤0.12 (Table 5). Between these values, results are considered "Indeterminate". Assessing the clinical agreement of the presumed positive and true negative samples, sensitivity of the assay was determined to be 89.5% (round-up to 90%) and Specificity was 99.9%. Positive and negative predictive values were 98.7% and 99.1%, respectively (Table 6; indeterminate samples removed). The numbers report for Table 6 represent the total of multiple repeated tests.

TABLE 5

Clinical agreement of validation study positive and negative samples, plus negative cross-reactivity samples following negative (NEG) call threshold ≤0.120 and positive (POS) call threshold of ≥0.389, with indeterminate (INDT) samples falling between these thresholds.

| Control type | n | # iterations | total tests | NEG | INDT | POS | FP | FN | Accuracy |
|---|---|---|---|---|---|---|---|---|---|
| Positive | 30 | 4 | 120 | 9 | 34 | 77 | | 9 | 89.53% |
| Negative | 32 | 4 | 128 | 127 | 1 | 0 | 0 | | 100% |
| Cross-Reactivity | 320 | 3 | 960 | 904 | 55 | 1 | 1 | | 99.89% |

FP = false positive;
FN = false negative.

TABLE 6

Clinical agreement of presumed positive and true negative samples with the assay following determined cut of values for presenting positive and negative results.

| | | COVID-19 (PCR+) | | |
|---|---|---|---|---|
| | | Positive | Negative | |
| Assay | Positive | 77 | 1 | Sensitivity = 89.53% Specificity = 99.90% Positive predictive value (PPV) = 98.72% |
| | Negative | 9 | 1031 | Negative predictive value (NPV) = 99.13% |

Evaluation of $OD_{630nm}$ Absorbance

To reduce incorrect result reporting due to inefficient absorbance or failed assay performance, $OD_{630nm}$ absorbance was evaluated for components of the ELISA assay. If unquenched, the TMB generates a wavelength of 630 nm (Table 7).

TABLE 7

Enzyme/Substrate Systems for ELISA

| | | Reading wavelength (nm) | |
|---|---|---|---|
| Enzyme label | System | Non-stopped | Stopped |
| Horseradish peroxidase (HRP) | OPD | 450 | 492 |
| | TMB | 630 | 450 |
| | ABTS | 414 | 414 |
| Alkaline Phosphatase (Alk-phos) | pNPP | 405 | 405 |
| β-Galactosidase (β-gal) | ONPG | 420 | 420 |
| Urease | Urea bromocresol | 588 | 588 |

OPD = O-phenylenediamine dihydrochloride; TMB = 3,3',5,5'-tetramethylbenzidine; ABTS = 2,2'-azinobis [3-ethylbenzothiazoline-6-sulfonic acid]-diammonium salt; pNPP = para-nitrophenylphosphate; and ONPG = ortho-nitrophenyl-β-galactoside.

A new protocol step after the last step of the ELISA was introduced, addition of sulfuric acid, where the plate was foil sealed and vortexed prior to being put on the plate reader. In addition, the average 630 reading across all validation study plates was taken and a threshold of 2 standard deviations above that was set as a threshold for result reporting; if a sample $OD_{630nm}$ reads above 0.05, the sample was rerun.

This addendum sets new thresholds for result reporting for the SARS-CoV-2 ELISA pan-Ig Antibody Test. The threshold for reporting negative results were samples with $OD_{450nm}$ of ≤0.120. The threshold for reporting positive results were samples with $OD_{450nm}$ of ≥0.389. Indeterminate results fell between the two thresholds. Each assay plate was run with a minimum of 12 negative serum controls and two positive and two NTC controls which met these expectations as a Quality Control measure for the plate results to be reported.

Example 3—Serological Assay for Spike Protein S2 Domain Antibodies

The previously validated SARS-CoV-2 serological assay utilizes the receptor binding domain (RBD) of the SARS-CoV-2 spike protein as a target in the ELISA assay. This RBD spike protein assay provided results via optical density (OD) which were used to classify patients as either POSITIVE, NEGATIVE or INDETERMINANT. To improve the accuracy of results reporting and resolve INDETERMINANT calls made using RBD spike, a secondary confirmation assay using the S2 protein as a target was developed and validated using a diagnostic validation sample set and supporting neutralization assays. Importantly, ELISA run conditions, protocol, instrumentation and sample dilution for the S2 assay remain identical to the previously validation RBD spike assay.

Methodology

The S2 protein was first run on the standard validation panel consisting of:
1) 30 PCR-confirmed positive serum samples from SARS-CoV-2 infected patients confirmed via rtPCR testing and collected at a minimum of 10 day following symptom onset.
2) 34 PCR-confirmed negative samples consisting of 32 serum samples collected prior to September of 2019 and 2 samples from symptomatic patients collected in March of 2020 but testing negative for SARS-CoV-2 using rtPCR testing.
3) 29 water samples.
4) 3 blank, NTC controls.

S2 was subsequently run on a cross-reactivity panel consisting of 240 presumed negative samples collected prior to the SARS-CoV-2 outbreak (September 2019), and going back as far as 5 years. This sample set was used to determine a threshold for calling S2 positive results and provide information on the overall cross-reactivity of the S2 protein. Neutralization assays were then performed on a sample set of 124 samples collected May 2020 that had previously been run for both RBD spike and S2 proteins to show correlation of neutralization with positive antibody results.

Results

Figure 8:
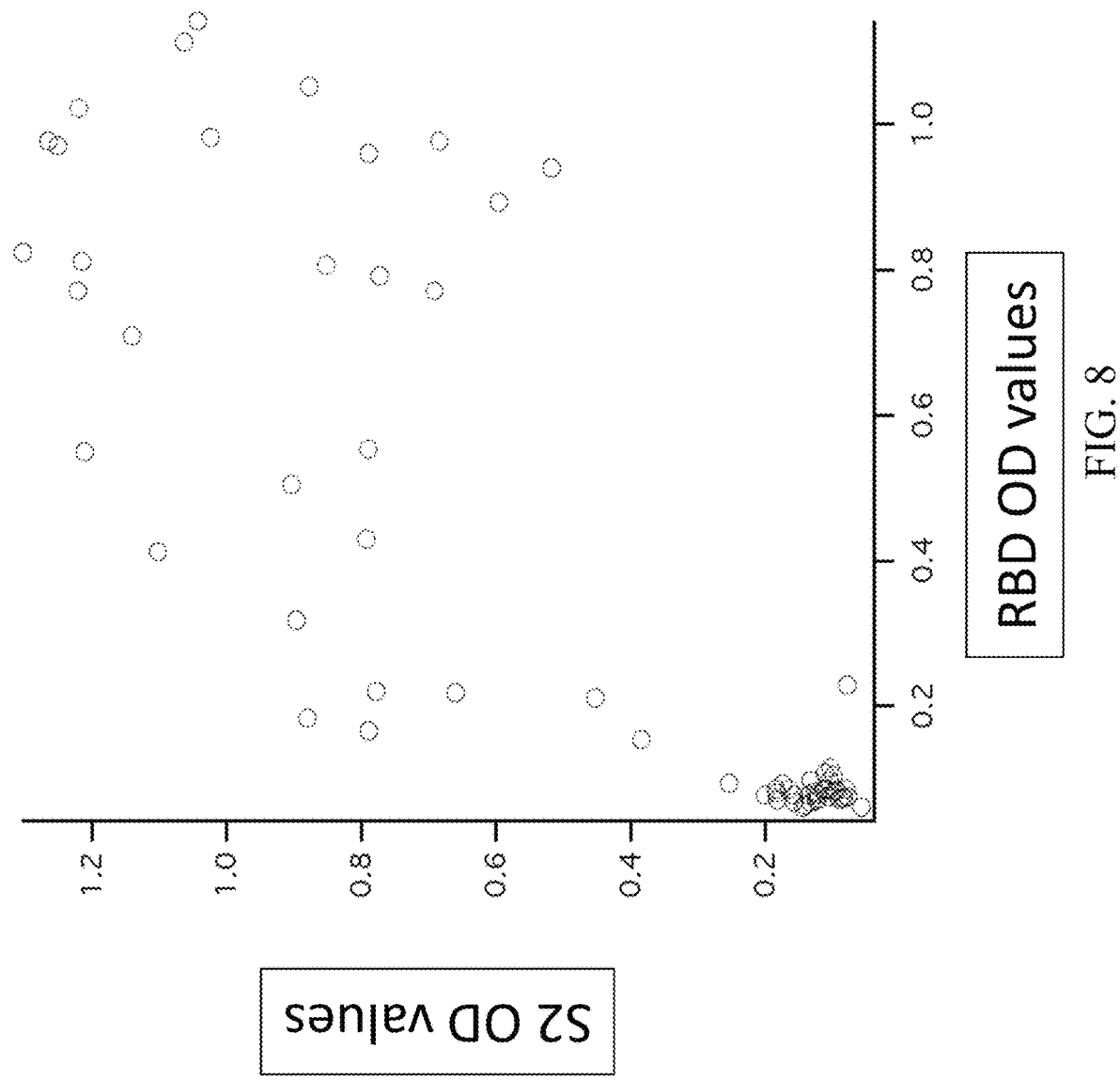

The resulting OD values using the S2 protein for the validation sample set were plotted against the OD values for the RBD spike protein and presented in FIG. 8. This figure shows all negative samples clustering at or below and OD of 0.2 for both RBD spike and S2 proteins. The average OD value for negative validation samples using S2 was 0.13 with a standard deviation of 0.04. The positive validation samples showed no direct correlation in OD value between S2 and RBD spike.

Figure 9:
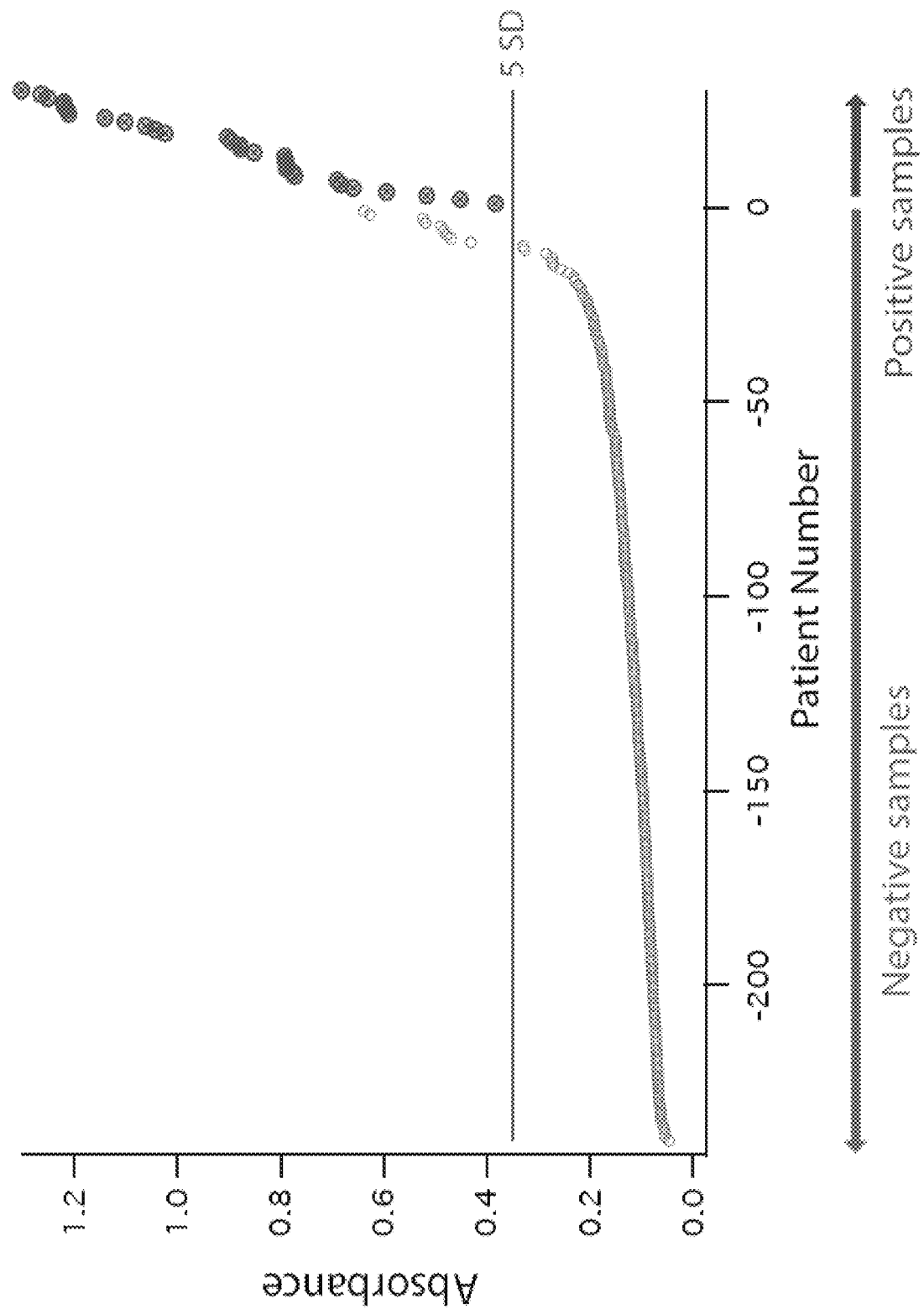

Resulting OD values for S2 runs on all 240 cross-reactivity panel samples showed a similar average and standard deviation (0.12 and 0.046 respectively) as the negatives on the validation sample, which were then combined with the positive samples from the validation plate and plotted in FIG. 9. Using 5 standard deviations as a cutoff for calling S2 POSITIVES resulted in a raw OD threshold of 0.35. Using this threshold, the S2 assay showed a cross-reactivity rate of approximately 3% generating 9 total positive calls out of a total of 262 presumed negatives and called all 30/30 rtPCR confirmed positives correctly.

Neutralization assays were then run on a cohort of 123 samples collected May 2020 that had been run for both RBD spike and S2 using the aforementioned cutoffs for calling positives (0.389 for RBD spike, 0.350 for S2) and indeterminates (0.120 for RBD spike) and is presented in Table 8 below. This data shows that all samples testing positive for both RBD spike and S2 neutralized the SARS-CoV-2 virus. While 2 total samples testing indeterminant for RBD spike and positive for S2 showed virus neutralization, 2 others showed neutralization and tested indeterminant for RBD spike and NEGATIVE for S2. Importantly, 6 samples testing positive for RBD spike but negative for S2 showed NO neutralization indicating they were likely false positives using the RBD spike assay results alone. No samples testing negative for both RBD spike and S2 showed neutralization.

TABLE 8

Sample cohort collected May 2020 for RBD spike, S2, and tested for SARS-CoV-2 neutralization. Samples represented in bold text indicate positive for neutralization, samples with S2 OD values represented in *bold italicized text* indicate positive for S2, samples represented in <u>bold underlined text</u> indicate positive for RBD spike, negative for S2, and negative for neutralization. Table is sorted by RBD spike OD, largest to smallest.

| Sample ID | PFU neutralized | SPIKE OD | S2 OD |
|---|---|---|---|
| REDCAP5878 | 100 | 1.222 | *0.873* |
| REDCAP9353 | 100 | 1.076 | *0.863* |
| REDCAP5928 | 100 | 1.034 | *0.83* |
| REDCAP1980 | 100 | 0.964 | *0.922* |
| REDCAP2728 | 100 | 0.915 | *0.644* |
| REDCAP2108 | 100 | 0.913 | *1.075* |
| REDCAP1780 | 100 | 0.898 | *0.916* |
| REDCAP1386 | 100 | 0.759 | *0.526* |
| REDCAP462 | 100 | 0.748 | *0.726* |
| REDCAP5760 | 100 | 0.728 | *0.493* |
| REDCAP7729 | 100 | 0.722 | *0.613* |
| REDCAP6620 | 100 | 0.702 | *0.603* |
| REDCAP5284 | 100 | 0.685 | *0.643* |
| REDCAP240 | 100 | 0.679 | *0.518* |
| REDCAP2593 | 100 | 0.616 | *0.692* |
| <u>REDCAP8770</u> | <u>0</u> | <u>0.598</u> | 0.144 |
| <u>REDCAP1961</u> | <u>0</u> | <u>0.58</u> | 0.1 |
| REDCAP3611 | 100 | 0.569 | *0.462* |
| REDCAP3055 | 100 | 0.566 | *0.882* |
| <u>REDCAP2110</u> | <u>0</u> | <u>0.536</u> | 0.18 |
| REDCAP2312 | 100 | 0.53 | *1.026* |
| <u>REDCAP6289A</u> | <u>0</u> | <u>0.462</u> | 0.123 |
| REDCAP194 | 100 | 0.442 | *0.439* |
| REDCAP5796 | 100 | 0.424 | *0.748* |
| <u>REDCAP6894</u> | <u>0</u> | <u>0.408</u> | 0.21 |
| <u>REDCAP5259</u> | <u>0</u> | <u>0.393</u> | 0.2 |
| REDCAP412 | 100 | 0.389 | *0.594* |
| POSITIVE THRESHOLD | | | |
| REDCAP16 | 0 | 0.355 | 0.133 |
| REDCAP4976 | 0 | 0.316 | *0.52* |
| REDCAP9481 | 0 | 0.311 | 0.1 |
| REDCAP296 | 0 | 0.307 | 0.084 |
| REDCAP406 | 0 | 0.3 | 0.107 |
| REDCAP5491 | 0 | 0.265 | 0.211 |
| REDCAP2034 | 0 | 0.263 | *0.44* |
| REDCAP2148 | 0 | 0.26 | 0.084 |
| REDCAP1324 | 0 | 0.231 | 0.093 |
| REDCAP8879 | 0 | 0.226 | 0.082 |
| REDCAP524 | 0 | 0.225 | 0.186 |
| REDCAP5987 | 0 | 0.224 | 0.177 |
| REDCAP5041 | 100 | 0.221 | 0.134 |
| REDCAP6354 | 0 | 0.214 | 0.192 |
| REDCAP6337A | 0 | 0.211 | 0.244 |
| REDCAP6158 | 0 | 0.21 | 0.114 |
| REDCAP4890 | 0 | 0.206 | *0.543* |
| REDCAP1581 | 0 | 0.201 | 0.252 |
| REDCAP7655 | 0 | 0.19 | 0.085 |
| REDCAP798A | 0 | 0.187 | 0.128 |

TABLE 8-continued

Sample cohort collected May 2020 for RBD spike, S2, and tested for SARS-CoV-2 neutralization. Samples represented in bold text indicate positive for neutralization, samples with S2 OD values represented in *bold italicized text* indicate positive for S2, samples represented in <u>bold underlined text</u> indicate positive for RBD spike, negative for S2, and negative for neutralization. Table is sorted by RBD spike OD, largest to smallest.

| Sample ID | PFU neutralized | SPIKE OD | S2 OD |
|---|---|---|---|
| REDCAP2855 | 0 | 0.186 | 0.095 |
| REDCAP1335 | 0 | 0.184 | 0.23 |
| REDCAP5108 | 0 | 0.184 | 0.13 |
| REDCAP2734 | 0 | 0.179 | 0.137 |
| REDCAP9159 | 0 | 0.178 | 0.181 |
| REDCAP4571 | 0 | 0.178 | 0.118 |
| REDCAP1157 | 100 | 0.175 | *0.715* |
| REDCAP3806 | 0 | 0.175 | 0.121 |
| REDCAP6275A | 0 | 0.174 | 0.138 |
| REDCAP8829 | 0 | 0.173 | 0.11 |
| REDCAP7114 | 0 | 0.169 | 0.182 |
| REDCAP4966 | 0 | 0.168 | 0.304 |
| REDCAP5890 | 0 | 0.162 | 0.166 |
| REDCAP4901 | 0 | 0.16 | 0.084 |
| REDCAP7846 | 100 | 0.158 | *0.427* |
| REDCAP6337A | 0 | 0.157 | 0.101 |
| REDCAP2607 | 0 | 0.153 | 0.135 |
| REDCAP3320 | 0 | 0.153 | 0.135 |
| REDCAP5460 | 0 | 0.152 | 0.236 |
| REDCAP5434 | 0 | 0.152 | 0.204 |
| REDCAP4271 | 0 | 0.152 | 0.187 |
| REDCAP6321A | 0 | 0.151 | 0.279 |
| REDCAP2483 | 0 | 0.151 | 0.239 |
| REDCAP1282 | 0 | 0.151 | 0.157 |
| REDCAP1312 | 0 | 0.15 | 0.1 |
| REDCAP413 | 0 | 0.147 | 0.174 |
| REDCAP465 | 0 | 0.146 | 0.143 |
| REDCAP10550 | 0 | 0.146 | 0.109 |
| REDCAP7530 | 0 | 0.146 | 0.098 |
| REDCAP897A | 0 | 0.146 | 0.077 |
| REDCAP10050 | 0 | 0.142 | 0.185 |
| REDCAP1935 | 0 | 0.142 | 0.151 |
| REDCAP2734 | 0 | 0.141 | 0.177 |
| REDCAP6578A | 0 | 0.141 | 0.174 |
| REDCAP873 | 0 | 0.14 | 0.309 |
| REDCAP1830 | 0 | 0.138 | 0.155 |
| REDCAP2035 | 0 | 0.138 | 0.148 |
| REDCAP2838 | 0 | 0.137 | 0.194 |
| REDCAP852 | 0 | 0.134 | 0.29 |
| REDCAP782A | 0 | 0.134 | 0.176 |
| REDCAP9605 | 0 | 0.133 | 0.296 |
| REDCAP10557 | 0 | 0.133 | 0.17 |
| REDCAP8739 | 0 | 0.133 | 0.156 |
| REDCAP8641 | 0 | 0.133 | 0.106 |
| REDCAP8602 | 0 | 0.13 | 0.185 |
| REDCAP3160 | 0 | 0.128 | 0.128 |
| REDCAP3139 | 0 | 0.128 | 0.116 |
| REDCAP9524 | 0 | 0.127 | 0.387 |
| REDCAP4206 | 0 | 0.127 | 0.136 |
| REDCAP292 | 0 | 0.127 | 0.091 |
| <u>REDCAP1849</u> | 0 | <u>0.126</u> | 0.118 |
| REDCAP10312 | 0 | 0.126 | 0.106 |
| REDCAP5767 | 0 | 0.123 | 0.128 |
| REDCAP2583 | 0 | 0.123 | 0.08 |
| REDCAP5368 | 0 | 0.121 | 0.088 |
| REDCAP6344A | 0 | 0.12 | 0.108 |
| REDCAP6170A | 0 | 0.12 | 0.106 |
| REDCAP8586 | 0 | 0.12 | 0.103 |
| INDETERMINANT THRESHOLD | | | |
| REDCAP10341 | 0 | 0.119 | 0.19 |
| REDCAP1885 | 0 | 0.118 | 0.291 |
| REDCAP2682 | 0 | 0.118 | 0.223 |
| REDCAP2641 | 0 | 0.118 | 0.144 |
| REDCAP10548 | 0 | 0.118 | 0.086 |
| REDCAP1994 | 0 | 0.114 | 0.268 |
| REDCAP7663 | 0 | 0.113 | 0.07 |
| REDCAP8417 | 0 | 0.112 | 0.071 |
| REDCAP6571 | 0 | 0.099 | 0.1 |
| REDCAP5297 | 0 | 0.09 | 0.163 |
| REDCAP3786 | 0 | 0.088 | 0.161 |
| REDCAP10431 | 0 | 0.088 | 0.094 |
| REDCAP1658 | 0 | 0.087 | 0.168 |
| REDCAP8941 | 0 | 0.085 | 0.139 |
| REDCAP10090 | 0 | 0.085 | 0.135 |
| REDCAP1245 | 0 | 0.084 | 0.114 |
| REDCAP287 | 0 | 0.08 | 0.163 |
| REDCAP6362 | 0 | 0.071 | 0.094 |

Conclusions

The performance of the S2 assay is sufficient for use as a secondary confirmation assay when run on samples subsequent to the initial RBD spike screening assay. Under these conditions, all samples testing positive or indeterminant for RBD spike are cherry picked and run for S2 as a secondary screen. This secondary confirmation testing and the resulting reporting algorithm detailed below in Table 9 improves the accuracy of true positive reporting to 10000 in this validation experiment. This new testing and reporting algorithm will be implemented immediately.

TABLE 9

Testing and reporting algorithm using S2 as secondary confirmation assay

| Assay | result | Assay | result | final report |
|---|---|---|---|---|
| RBD spike | POSITIVE | S2 | POSITIVE | POSITIVE |
| RBD spike | POSITIVE | S2 | NEGATIVE | NEGATIVE |
| RBD spike | INDETERMINANT | S2 | POSITIVE | INDETERMINANT |
| RBD spike | INDETERMINANT | S2 | NEGATIVE | NEGATIVE |
| RBD spike | NEGATIVE | N/A | N/A | NEGATIVE |

The invention claimed is:

1. A test system comprising:

a first surface comprising a first antigen comprising an amino acid sequence that has at least 99% identity to the amino acid sequence of the severe acute respiratory syndrome coronavirus 2 (SARS-CoV-2) receptor binding domain (RBD) antigen set forth in SEQ ID NO: 1; and a second surface comprising a second antigen comprising an amino acid sequence that has at least 99% identity to the amino acid sequence of the SARS-CoV-2 S2 antigen set forth in SEQ ID NO: 3, one or more first binding moieties that specifically bind to a constant region of human IgG, one or more second binding moieties that specifically bind to a constant region of human IgA and one or more third binding moieties that specifically bind to a constant region of human IgM.

2. The test system of claim 1, wherein the first antigen comprises the amino acid sequence of SARS-CoV-2 RBD antigen set forth in SEQ ID NO: 1.

3. The test system of claim 1, wherein the second antigen comprises the amino acid sequence of SARS-CoV-2 S2 antigen set forth in SEQ ID NO: 3.

4. The test system of claim 1, wherein the binding moieties are antibodies.

5. The test system of claim 1, wherein the first, second and third binding moieties further comprise a detectable moiety.

6. The test system of claim 1, wherein the first surface is substantially free from full-length SARS-CoV-2 spike protein.

7. The test system of claim 1, wherein the first surface is substantially free from a fragment of full-length SARS-CoV-2 S1 protein greater than 300 amino acids in length or a fragment of full-length SARS-CoV-2 S1 protein that does not comprise the RBD.

8. The test system of claim 1, wherein the second surface is substantially free from full-length SARS-CoV-2 spike protein.

9. The test system of claim 1, wherein the second surface is substantially free from full-length SARS-CoV-2 S1 protein.

10. A kit, comprising the test system of claim 1, comprising:

the first antigen; the second antigen; and the first binding moiety, the second binding moiety, and the third binding moiety, in separate containers.

11. A test system comprising:

a first well comprising:

an immobilized first binding moiety that specifically binds to a constant region of human IgG, an immobilized second binding moiety that specifically binds to a constant region of human IgA and an immobilized third binding moiety that specifically binds to a constant region of human IgM;
 a first biological sample from a host; and
 a first antigen comprising an amino acid sequence that has at least 99% identity to the amino acid sequence of the severe acute respiratory syndrome coronavirus 2 (SARS-CoV-2) receptor binding domain (RBD) antigen set forth in SEQ ID NO: 1, wherein the first antigen comprises a detectable moiety;
and
a second well comprising:
 an immobilized first binding moiety that specifically binds to a constant region of human IgG, an immobilized second binding moiety that specifically binds to a constant region of human IgA and an immobilized third binding moiety that specifically binds to a constant region of human IgM;
 a second biological sample from the host; and
 a second antigen an amino acid sequence that has at least 99% identity to the amino acid sequence of the SARS-CoV-2 S2 antigen set forth in SEQ ID NO: 3, wherein the second antigen comprises a detectable moiety.

12. A method for detecting the presence of host antigen-specific antibodies that specifically bind SARS-CoV-2, the method comprising the steps of:
1) exposing a first biological sample from the host to a first surface comprising a first antigen comprising an amino acid sequence that has at least 99% identity to the amino acid sequence of the severe acute respiratory syndrome coronavirus 2 (SARS-CoV-2) receptor binding domain (RBD) antigen set forth in SEQ ID NO: 1;
2) incubating the first surface with a first binding moiety that specifically binds to a constant region of human IgG, a second binding moiety that specifically binds to a constant region of human IgA and a third binding moiety that specifically binds to a constant region of human IgM;
3) detecting binding of one or more of the first, second and third binding moieties at the first surface to host antigen-specific antibodies, which generates a first signal;
4) exposing a second biological sample from the host to a second surface comprising a second antigen an amino acid sequence that has at least 99% identity to the amino acid sequence of the SARS-CoV-2 S2 antigen set forth in SEQ ID NO: 3;
5) incubating the first surface with a fourth binding moiety that specifically binds to a constant region of human IgG, a fifth binding moiety that specifically binds to a constant region of human IgA and a sixth binding moiety that specifically binds to a constant region of human IgM; and
6) detecting binding of one or more of the fourth, fifth and sixth binding moieties at the second surface to host antigen-specific antibodies, which generates a second signal,
thereby detecting the presence of host antigen-specific antibodies that specifically bind SARS-CoV-2.

13. The method of claim 12, wherein the first antigen comprises the amino acid sequence of SARS-CoV-2 RBD antigen set forth in SEQ ID NO: 1.

14. The method of claim 12, wherein the second antigen comprises the amino acid sequence of SARS-CoV-2 S2 antigen set forth in SEQ ID NO: 3.

15. The method of claim 12, wherein the binding moieties are antibodies.

16. The method of claim 12, wherein the first, second, third, fourth, fifth and sixth binding moieties further comprise a detectable moiety.

17. The method of claim 16, wherein the detectable moiety is a chromogenic label.

18. The method of claim 17, wherein the chromogenic label comprises horseradish peroxidase (HRP).

19. The method of claim 18, wherein incubation of the first, second and third binding moieties with an HRP substrate produces a colorimetric signal.

20. The method of claim 12, wherein the first surface is substantially free from full-length SARS-CoV-2 spike protein.

21. The method of claim 12, wherein the first surface is substantially free from a fragment of full-length SARS-CoV-2 S1 protein greater than 300 amino acids in length or a fragment of full-length SARS-CoV-2 S1 protein that does not comprise the RBD.

22. The method of claim 12, wherein the second surface is substantially free from full-length SARS-CoV-2 spike protein.

23. The method of claim 12, wherein the second surface is substantially free from full-length SARS-CoV-2 S1 protein.

24. The method of claim 12, wherein the first binding moiety is the same as the fourth binding moiety, the second binding moiety is the same as the fifth binding moiety and/or the third binding moiety is the same as the sixth binding moiety.

25. The method of claim 12, wherein the biological sample is selected from the group consisting of serum, blood, plasma, sputum, urine, semen, mucous, sweat and tears.

26. The method of claim 12, wherein:
 a first signal value that is at least five standard deviations above a negative control sample indicates a first positive result;
 a first signal value that is at least three standard deviations but less than five standard deviations above a negative control sample indicates a first indeterminate result;
 a first signal value that is less than three standard deviations above a negative control sample indicates a first negative result;
 a second signal value that is at least five standard deviations above a negative control sample indicates a second positive result;
 a second signal value that is at least three standard deviations but less than five standard deviations above a negative control sample indicates a second indeterminate result; and
 a second signal value that is less than three standard deviations above a negative control sample indicates a second negative result.

27. The method of claim 26, wherein a first positive result and a second positive result indicates the presence of host antigen-specific antibodies.

28. The method of claim 26, wherein a first positive result and a second indeterminate result indicates the presence of host antigen-specific antibodies.

29. The method of claim 26, wherein a first positive result and a second negative result indicates an absence of host antigen-specific antibodies.

30. The method of claim 26, wherein a first indeterminate result and a second negative result indicates an absence of host antigen-specific antibodies.

* * * * *